(12) United States Patent
Huizenga et al.

(10) Patent No.: US 8,068,894 B2
(45) Date of Patent: *Nov. 29, 2011

(54) AUTOMATED METHODS AND SYSTEMS FOR VASCULAR PLAQUE DETECTION AND ANALYSIS

(75) Inventors: Joel T. Huizenga, La Jollla, CA (US); Russell W. Anderson, Avondale, PA (US); Thomas Woodley Botherton, Poway, CA (US)

(73) Assignee: Ischem Corporation, La Jolla, CA (US)

( * ) Notice: Subject to any disclaimer, the term of this patent is extended or adjusted under 35 U.S.C. 154(b) by 284 days.

This patent is subject to a terminal disclaimer.

(21) Appl. No.: 12/541,855

(22) Filed: Aug. 14, 2009

(65) Prior Publication Data

US 2010/0185079 A1    Jul. 22, 2010

Related U.S. Application Data

(63) Continuation of application No. 10/923,124, filed on Aug. 21, 2004, now Pat. No. 7,657,299.

(60) Provisional application No. 60/497,375, filed on Aug. 21, 2003.

(51) Int. Cl.
*A61B 5/055*     (2006.01)
*G06K 9/36*      (2006.01)

(52) U.S. Cl. ........................... 600/410; 382/276

(58) Field of Classification Search .................. 600/407; 382/276

See application file for complete search history.

(56) References Cited

U.S. PATENT DOCUMENTS

| | | |
|---|---|---|
| 4,945,478 A | 7/1990 | Merickel et al. |
| 5,003,979 A | 4/1991 | Merickel et al. |
| 5,893,069 A | 4/1999 | White, Jr. |
| 6,088,676 A | 7/2000 | White, Jr. |
| 6,200,268 B1 | 3/2001 | Vince et al. |
| 6,231,834 B1 | 5/2001 | Unger et al. |
| 6,375,925 B1 | 4/2002 | Tsimikas et al. |
| 6,443,894 B1 | 9/2002 | Sumanaweera et al. |
| 6,507,747 B1 | 1/2003 | Gowda et al. |
| 6,615,071 B1 | 9/2003 | Casscells et al. |
| 6,922,462 B2 | 7/2005 | Acharya et al. |
| 6,928,142 B2 | 8/2005 | Shao et al. |
| 7,031,426 B2 | 4/2006 | Iatrou et al. |
| 7,082,325 B2 | 7/2006 | Hashimshony et al. |
| 7,175,597 B2 | 2/2007 | Vince et al. |
| 7,260,249 B2 | 8/2007 | Smith |
| 7,315,756 B2 | 1/2008 | Yarnykh et al. |
| 7,338,452 B2 | 3/2008 | Shiina et al. |
| 7,353,117 B2 | 4/2008 | Yuan et al. |

(Continued)

FOREIGN PATENT DOCUMENTS

WO    WO 2004-069027 A2    8/2004

OTHER PUBLICATIONS

Anderson et al., Automated classification of atherosclerotic plaque from magnetic resonance images using predictive models, Biosystems, 2007, pp. 456-466, vol. 90, Iss. 2.

(Continued)

*Primary Examiner* — Michael Rozanski
(74) *Attorney, Agent, or Firm* — Acuity Law Group, P.C.; Daniel M. Chambers

(57) ABSTRACT

Automated methods and systems for the detection and analysis of plaque in one or more regions of a patient's vasculature are described.

13 Claims, 14 Drawing Sheets

U.S. PATENT DOCUMENTS

| | | | |
|---|---|---|---|
| 7,356,367 | B2 | 4/2008 | Liang et al. |
| 7,369,887 | B2 | 5/2008 | Fayad et al. |
| 7,570,983 | B2 | 8/2009 | Becker |
| 2003/0211036 | A1 | 11/2003 | Degani et al. |
| 2004/0047497 | A1 | 3/2004 | Daw et al. |
| 2004/0061889 | A1 | 4/2004 | Wood et al. |
| 2004/0133098 | A1 | 7/2004 | Yarnykh et al. |
| 2004/0142496 | A1 | 7/2004 | Nicholson et al. |
| 2004/0243022 | A1 | 12/2004 | Carney et al. |
| 2004/0260170 | A1 | 12/2004 | Wood et al. |
| 2004/0265393 | A1 | 12/2004 | Unger et al. |
| 2004/0267110 | A1 | 12/2004 | Tremble |
| 2005/0038342 | A1 | 2/2005 | Mozayeni et al. |

OTHER PUBLICATIONS

Bishop, Neural Component Analysis, 1995, Clarendon Press, Oxford, Great Britain, United Kingdom, Table of Contents Only.

Gonzalez et al. (Ed.), Digital Image Processing 2nd Edition, 2002, Prentice-Hall, Inc., New Jersey, USA, Table of Contents Only.

Anderson et al., "Estimation of Spatio-temporal Neural Activity Using Radial Basis Function Networks," J. Computational Neuroscience 5(4):421-441 (1998).

Anderson et al., "Two-dimensional saccade-related population activity in superior colliculus in monkey," J. Nerophysiol. 80(2):798-817 (1998).

Baxt et al., "Bootstrapping confidence intervals for clinical input variable effects in a network trained to identify the presence of acute myocardial infarction," Neur. Comp. 7(3):624-638 (1995).

Bell et al., "Independent component analysis," Neural Comput. 7(6):1129-1159 (1995).

Botnar et al., "Noninvasive coronary vessel wall and plaque imaging with magnetic resonance imaging," Circulation 102(21):2582-2587 (2000).

Brotherton et al., "Application of neural nets to feature fusion," Proc. 26th Asilomar Conf. on Signals, Sys. Comp. 2:781-785 (1992).

Brotherton et al., "Application of time-frequency and time-scale representations to fault detection and classification," Proc. IEEE-SP Int'l Symp. On Time-Freq. Time-Scale Anal. 4:95-98 (1992).

Brotherton et al., "Classifying tissue structure in echocardiograms," IEEE Eng. Med. Bio. 13(5):754-760 (1994).

Brotherton et al., "Classifier design using evolutionary programming," Third Ann. Conf. Evol. Prog. 68-75 (1994).

Brotherton et al., "Information extraction from 2D electrophoresis images," Proc. of the 20th Ann. Con. of the IEEE Eng. Med. Bio. Soc. (EMBS '98) 2(2):1060-1063 (1998).

Brotherton et al., "The Application of Time-Frequency and Wavelets to Medical Ultrasound," Time-Frequency and Wavelets in Biomed. Eng. Ch. 3:1-33 (1998).

Cai et al., "Classification of human carotid atherosclerotic lesions with In Vivo multicontrast magnetic resonance imaging," Circulation 106(11):1368-1373 (2002).

Corti et al., "Artery dissection and arterial thrombus aging: the role of noninvasive magnetic resonance imaging," Circulation 103(19):2420-2421 (2001).

Corti et al., "Effects of lipid-lowering by simvastatin on human atherosclerotic lesions: A longitudinal study by high-resolution, noninvasive magnetic resonance imaging," Circulation 104(3):249-252 (2001).

Corti et al., "Lipid lowering by simvastatin induces regression of human atherosclerotic lesions: Two year's follow-up by high-resolution noninvasive magnetic resonance imaging," Circulation 106(23):2884-2887 (2002).

Cybenko, "Approximation by superpositions of a sigmoidal function," Mathematical Contl. Signal Systems 2(4):303-314 (1989).

Dhawan, Medical Image Analysis, IEEE Press Wiley-Interscience, Hoboken, NJ (2003).

Dowla et al., "Seismic discrimination with artificial neutral networks: preliminary results with regional spectral data," Bull. Seismo. Soc. Amer. 80(5):1346-1373 (1990).

Falk et al., "Coronary plaque disruption," Circulation 92(3):657-671 (1995).

Fayad et al., "In vivo magnetic resonance evaluation of atherosclerotic plaques in the human thoracic aorta: a comparison with transesophageal echocardiography," Circulation 101(21):2503-2509 (2000).

Fayad et al., "Noninvasive in vivo human coronary artery lumen and wall imaging using black-blood magnetic resonance imaging," Circulation 102(5):506-510 (2000).

Fayad et al., "Clinical imaging of the high-risk or vulnerable atherosclerotic plaque," Circ. Res. 89(4):305-316 (2001).

Fayad, "MR imaging for the noninvasive assessment of atherothrombotic plaques," Magn. Reson. Imaging Clin. N. Am. 11(1):101-113 (2003).

Froning et al., "Classification of CAD severity using fusion neural net analysis of multiple exercise ECG waveform representations," Proc. of Comp. in Cardio. 605-608 (1995) (Abstract Only).

Gallant et al., Unified Theory of Estimation and Inference for Nonlinear Dynamic Models, Oxford: Basil Blackwell (1988).

Goodenday et al., "Identifying coronary stenosis using an image-recognition neural network," IEEE Eng. Med. Biol. Mag. 16(5):139-144 (1997).

Han et al., "A multi-scale method for atomatic correction of intensity non-uniformity in MR images," J. Mag. Res. Imaging 13(3):428-436 (2001).

Han et al., "Detecting objects in image sequences using rule-based control in an active contour model," IEEE Trans. Biomed. Eng. 50(6):705-710 (2003).

Haralick, "Statistical and structural approaches to texture," Proc. IEEE 67 (5):786-804 (1979).

Hatsukami et al., "Visualization of fibrous cap thickness and rupture in human atherosclerotic carotid plaque in vivo with high-resolution, noninvasive magnetic resonance imaging," Circulation 102(9):959-964 (2000).

Helft et al., "Atherosclerotic aortic component quantification by noninvasive magnetic resonance imagin: an in vivo study in rabbits," J. Amer. Col. Cardiol. 37(4):1149-1154 (2001).

Hornik et al., "Multilayer feed forward networks are universal approximators," Neural Networks 2(5):359-366 (1989).

Itskovich et al., "Quantification of human atherosclerotic plaques using spatially enhanced cluster analysis of multicontrast-weighted magnetic resonance images," Magn. Reson. Med. 52(3):515-523 (2004).

Jang et al., "Functional equivalence between radial basis function networks and fuzzy inference systems," IEEE Trans. Neural Networks 4(1):156-159 (1993).

Kerwin et al., "A quantitative vascular analysis system for evaluation of atherosclerotic lesions by MRI," Medical Imaging and Computing, 4th International Conf. 1-8 (2001).

Kerwin et al., "Noise and motion correction in dynamic contrast-enhanced MRI for analysis of atherosclerotic lesions," Mag. Res. In Med. 47(6):1211-1217 (2002).

Maynor et al., "Chemical shift imaging of atherosclerosis at 7.0 telsa," Invest. Radiol. 24(1):52-60 (1989) (Abstract Only).

Merickel et al., "Identification and 3-D quantification of atherosclerosis using magnetic resonance imaging," Comput. Biol. Med. 18(2):89-102 (1995) (Abstract Only).

Mitsumori et al., "In Vivo accuracy of multisequence MR imaging for identifying unstable fibrous caps in advanced human carotid plaques," J. MRI 17:410-420 (2003).

Moody et al., "Fast learning in networks of locally-tuned processing units," Neural Comput. 1(2):281-294 (1989).

Naghavi et al., "New developments in the diction of vulnerable plaque," 3(2):125-135 Curr. Atheroscl. Rep. (2001).

Perez-Amaral et al., "A flexible tool for model building: The relevant transformation of the inputs network approach (RETINA)," Oxford Bulletin of Economics and Statistics 65(s1):821-838 (2002).

Richardson et al., "Influence of plaque configuration and stress distribution on fissuring coronary atherosclerotic plaques," Lancet 2(8669):941-944 (1989).

Sakata et al., "High Breakdown Point Conditional Dispersion Estimation with Application to S&P 500 Daily Returns Volatility," Econometrica 66(3):529-568 (1998).

Shinnar et al., "The diagnostic accuracy of Ex Vivo MRI for human atherosclerotic plaque characterization," Arterioscler. Throm. Vasc. Biol. 19:2756-2761 (1999).

Simpson, "Fuzzy Min-Max neural networks—Part 1: Classification," IEEE Trans. On Neural Networks 3(5):776-786 (1992).

Simpson, "Fuzzy Min-Max neural networks—Part 2: Clustering," IEEE Trans. On Fuzzy Systems 1(1):32-45 (1993).

Soila et al., "Proton relaxation times in arterial wall and atheromatous lesions in man," Invest. Radiol. 21(5):411-415 (1986) (Abstract Only).

Sullivan et al., "Data Snooping, Technical Trading Rule Performance, and the Bootstrap," J. of Finance 54(5):1647-1691 (1999).

Swanson et al., "A Model Selection Approach to Real-Time Macroeconomic Forecasting using Linear Models and Artificial Neural Networks," Rev. Econ. Stat. 79(4):540-550 (1997).

Toussaint et al., "Magnetic resonance images lipid, fibrous, calcified, hemorrhagic, thrombotic components of human atherosclerosis in vivo," Circulation 94(5):932-938 (1996).

Van Der Wal et al., "Site of intimal rupture of erosion of thrombosed coronary atherosclerotic plaques is characterized by an inflammatory process irrespective of the dominant plaque morphology," Circulation 89(1):36-44 (1994).

Viola et al., "Alignment by maximization of mutual information," Fifth Intl. Conference on Computer Vision 16-23 (1995).

Wells et al., "Multi-modal volume registration by maximization of mutual information," Med. Image Anal. 1(1):35-51 (1996).

White, "Learning in Artificial neural networks: A statistical perspective," Neural Comput. 1(4):425-464 (1989).

White, "Personal Readiness: Neural Network Modeling of Performance-Based Estimates," Office of Naval Research NeuralNet R&D Associates 1-68 (1999).

White, "A reality check for data snooping," Econometrica 68(5):1097-1126 (2000).

Woods et al., "Automated image registration: 1. General methods and intrasubject, intramodality validation," J. of Computer Assisted Tomography 22(1):139-152 (1998).

Worthley et al., "Noninvasive in vivo magnetic resonance imaging of experimental coronary artery lesions in a porcine model," Circulation 10(25):2956-2964 (2000).

Worthley et al., "Cardiac gated breath-hold black blood MRI of the coronary artery wall: an in vivo and ex vivo comparison," Intl. J. Cardiovas. Imaging 17(3):195-201 (2001).

Xu, "Gradient vector flow: A new external force for snakes," IEEE Proc. Conf. on Comp. Vis. Patt. Recog. 66-71 (1997).

Xu, "Snakes, shapes and gradient vector flow," IEEE Transactions on Image Processing 7(3):359-369 (1998).

Xu, "Atherosclerotic blood vessel tracking and lumen segmentation in topology changes situations of mr image sequences," Image Processing, 2000. Proceedings. 2000 International Conference 1:637-640 (2000).

Xu et al., "Segmentation of multi-channel image with Markov random field based active contour model," J. VSL1 Signal Processing 31(1):45-55 (2002).

Yang et al., "Segmentation of wall and plaque in In-Vitro vascular MR imaging," Intl. J. Cardiovasc. Imaging 19(5):419-428 (2003).

Yuan et al., "Measurement of atherosclerotic carotid plaque size in vivo using high-resolution magnetic resonance imaging," Circulation 98(24):2666-2671 (1998).

Yuan et al., "In Vivo Accuracy of Multispectral Magnetic Resonance Imaging for Identifying Lipid-Rich Necrotic Cores and Intraplaque Hemorrhage in Advanced Human Carotid Plaques," Circulation 104(17):2051-2056 (2001).

Zaman et al., "The role of plaque rupture and thrombosis in coronary artery disease," Atherosclerosis 149(2):251-266 (2000).

Zhao et al., "Effects of Prolonged Intensive Lipid-Lowering Therapy on the Characteristics of Carotid Atherosclerotic Plaques In Vivo by MRI A Case-Control Study," Thromb. Vasc. Biol. 21:1623-1629 (2001).

Original illumination gradient
Histogram Equalization
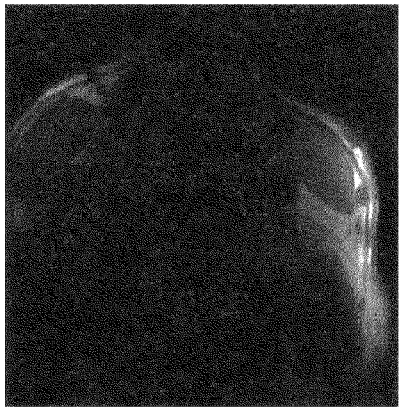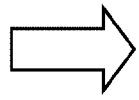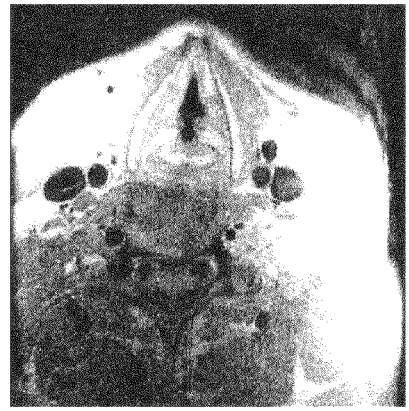
FIG.2A
FIG.2B MRI Images 510 PDW (Green)   520 T1W (Red)   530 T2W (Blue)

540 False color image 3-color image

550

Histopathology (validation)

Muscle wall tracing using gradient vector flow

Muscle wall tracing using gradient vector flow

AUTOMATED METHODS AND SYSTEMS FOR VASCULAR PLAQUE DETECTION AND ANALYSIS

RELATED APPLICATIONS

This patent application claims priority to, and the benefit of, each of the following patent applications: U.S. provisional patent application No. 60/497,375, filed 21 Aug. 2003; and U.S. non-provisional patent application Ser. No. 10/923,124, filed 21 Aug. 2004, each of which is hereby incorporated in its entirety for all purposes.

TECHNICAL FIELD

This invention concerns methods, software, and systems for the automated analysis of medical imaging data. Specifically, it concerns methods, software, and systems for the automated detection and analysis of plaque within part or all of a patient's vasculature.

BACKGROUND OF THE INVENTION

1. Introduction

The following description includes information that may be useful in understanding the present invention. It is not an admission that any such information is prior art, or relevant, to the presently claimed inventions, or that any publication specifically or implicitly referenced is prior art.

2. Background

Atherosclerosis is the most common cause of ischemic heart disease. When considered separately, stroke is the third leading cause of death, with the vast majority of strokes being the result of ischemic events. However, arteriosclerosis is a quite common inflammatory response, and atherosclerosis without thrombosis is in general a benign disease. Several studies indicate that the plaque composition rather than the degree of stenosis is the key factor for predicting vulnerability to rupture or thrombosis. Such thrombosis-prone or high-risk plaques are referred to as "vulnerable" plaques.

Plaque rupture is triggered by mechanical events, but plaque vulnerability is due to weakening of the fibrous cap, interplaque hemorrhage, and softening of plaque components, often as a result of infection and macrophage and T-cell infiltration. In general, lipid-rich, soft plaques are more prone to rupture than collagen-rich, hard plaques. Several morphological and physiological features are associated with vulnerable and stable plaque. Morphological characteristics suggest structural weakness or damage (thin or ruptured fibrous cap, calcification, negative remodeling, neovascularization, large lipid deposits, etc.), while physiological features suggest chemical composition, active infection, inflammatory responses, and metabolism. Many of the factors are subjective or qualitative, reflecting the fact that not all characteristics have been validated as risk determinants. The validation of risk factors requires long-term longitudinal clinical studies, endarterectomies, or autopsies.

Several invasive methods have been used to identify vulnerable plaque, including intravenous ultrasound (IVUS), angioscopy, intravascular MR, and thermography. Since invasive methods expose the patient to significant risk of stroke and MI, they are not appropriate for screening or serial examination. Finally, since these methods require the use of a catheter, estimates of overall vascular plaque burden must be extrapolated from examination of only a few local plaque deposits. Moreover, due to physical constraints such as catheter and artery size, arterial branching, etc., much of a patient's vasculature is inaccessible to invasive instruments.

While MRI has been used to identify morphological plaque features, such as plaque size and fibrous cap thickness, with high sensitivity and specificity, most efforts to characterize plaque involve visual inspection of CAT or MRI scans by expert radiologists. This is a time-consuming (and thus expensive) and error-prone process, subject to several subjective biases, not least that humans are notoriously poor at simultaneously assessing statistical relationships between more than two or three variables. A natural tendency is to focus on gross boundaries and local textures. When considering multimodal images, this problem is multiplied severalfold because in order to digest all the available evidence, the analyst has to assess, pixel-by-pixel, the local environment in as many as four distinct modalities. Typically, this forces the analyst to concentrate on only one modality, with the "best" contrast for a particular tissue, and disregard potential contrary evidence in the other modalities. Classification accuracy is subject to variability between researchers and even for the same researcher over time, making a standardized diagnostic test virtually impossible. In most cases, validation of the interpreted image can only be accomplished by histological examination of endarterectomies.

Given these importance of plaque detection and analysis to patient health, there is a clear need for improved methods for the detection and analysis of plaque in vivo.

3. Definitions

Before describing the instant invention in detail, several terms used in the context of the present invention will be defined. In addition to these terms, others are defined elsewhere in the specification, as necessary. Unless otherwise expressly defined herein, terms of art used in this specification will have their art-recognized meanings.

A "medical imaging system" refers to any system that can be used to gather, process, and generate images of some or all of the internal regions a patient's body. Typically such systems include a device to generate and gather data, as well as a computer configured to process and analyze data, and frequently generate output images representing the data. Devices used to generate and gather data include those that are non-invasive, e.g., magnetic resonance imaging ("MRI") machines, positron emission tomography ("PET") machines, computerized axial tomography ("CAT") machines, ultrasound machines, etc., as well as devices that generate and collect data invasively, e.g., endoscopes (for transmission of visual images from inside a cavity or lumen in the body) and catheters with a sensing capability. Data collected from such devices are then transmitted to a processor, which in at least some cases, can be used to produce images of one or more internal regions of the patient's body. A healthcare professional trained to interpret the images then examines and interprets the images to generate a diagnosis or prognosis.

A "patentable" composition, process, machine, article of manufacture, or improvement according to the invention means that the subject matter satisfies all statutory requirements for patentability at the time the analysis is performed. For example, with regard to novelty, non-obviousness, or the like, if later investigation reveals that one or more claims encompass one or more embodiments that would negate novelty, non-obviousness, etc., the claim(s), being limited by definition to "patentable" embodiments, specifically exclude the unpatentable embodiment(s). Also, the claims appended hereto are to be interpreted both to provide the broadest reasonable scope, as well as to preserve their validity. Furthermore, if one or more of the statutory requirements for patentability are amended or if the standards change for assessing whether a particular statutory requirement for patentability is satisfied from the time this application is filed or issues as a patent to a time the validity of one or more of the appended claims is questioned, the claims are to be interpreted in a way that (1) preserves their validity and (2) provides the broadest reasonable interpretation under the circumstances.

The term "treatment" or "treating" means any treatment of a disease or disorder, including preventing or protecting against the disease or disorder (that is, causing the clinical symptoms (or the underlying process that may produce or contribute to the symptoms) not to develop); inhibiting the disease or disorder (i.e., arresting or suppressing the development of clinical symptoms, or suppressing progression of one or more underlying process that contributes to the pathology that may produce symptoms); and/or relieving the disease or disorder (i.e., causing the regression of clinical symptoms; or regression of one or more processes that contribute to the symptoms). As will be appreciated, it is not always possible to distinguish between "preventing" and "suppressing" a disease or disorder since the ultimate inductive event or events may be unknown or latent. Accordingly, the term "prophylaxis" will be understood to constitute a type of "treatment" that encompasses either or both "preventing" and/or "suppressing". The term "protection" thus includes "prophylaxis".

SUMMARY OF THE INVENTION

It is an object of this invention to provide patentable methods, software, and systems for the automated detection and, if desired, analysis of plaque in one or more regions of a patient's vasculature obtained from data from a medical imaging system, or the initial sensing or data collection processes such as (but not limited to) those that could be used to generate an image.

Thus, in one aspect, the invention concerns automated methods of assessing a degree of atherosclerosis in at least a portion of a patient's vasculature, frequently in part of all of one or more blood vessels, particularly those that supply blood to an organ such as the brain, heart, kidney, liver, lungs, intestines, bladder, stomach, ovaries, and testes, as well as to the periphery, such as the arms and legs. Preferred blood vessels for analysis include the carotid arteries, coronary arteries, and the aorta. While the instant methods can be used to detect and analyze vascular plaque in a variety of animal, the methods will most frequently be used on humans.

Typically, the instant methods comprise computationally processing processable data from at least one cross section (or portion thereof) of at least one blood vessel of a patient's vasculature derived from a medical imaging system to determine if the blood vessel (or at least the part under analysis) comprises at least one plaque component or tissue correlated with the presence of plaque. Performance of such methods thus allows assessment of one or measures related to atherosclerosis in at least a portion of the patient's vasculature.

In preferred embodiments, these methods allow a determination of whether a blood vessel contains plaque, particularly plaque vulnerable to rupture. For a particular cross section, the data analyzed may comprise some or all of the data initially collected. The medical imaging system used to obtain the initial data may be an invasive or non-invasive imaging system. Preferred non-invasive imaging system comprises one or more MRI, CT, PET, thermography, or ultrasound instruments. Instruments that include multiple non-invasive imaging functionalities can also be employed. Preferred invasive instruments include catheters equipped with one or more sensors. Examples include catheters for intravenous ultrasound, angioscopy, intravascular MR, and thermography. Data from invasive and non-invasive imaging techniques can also be combined for analysis. Similarly, other or additional data may also be included, for example, data obtained from the use of contrast agents, labeling moieties specific for one or more tissues, cell types, or ligands that, for example, comprise tissues or components of healthy or diseased vasculature, including plaque or components thereof.

MRI-based methods represent a preferred set of embodiments. In such embodiments, an MRI instrument is used to generate raw magnetic resonance data from which processable magnetic resonance data are derived. One or more different imaging modalities, implemented by one or more different radio frequency pulse sequence series, can allow different tissues and tissue components to be distinguished upon subsequent analysis. Preferred data types generated by such modalities include T1-weighted data, T2-weighted data, PDW-weighted data, and TOF-weighted data. Data generated by combinations of one or more of these and other data types may also be combined.

While performing the methods of the invention, it may be desirable to pre-process and/or normalize data. In any event, the processable data are computationally processed to determine whether the blood vessel, in the region of the cross section(s) (or portion(s) thereof) comprise artery and plaque tissue or components thereof. In preferred embodiments, tissue or component type determination is accomplished by comparing by computer different tissue types identified in the data to one or more of statistical classifiers. Such classifiers can be developed using known outcome data (e.g., by post-operative histological examination, direct tissue inspection, or labeling by one or more experts) by any suitable process, including logistic regression, decision trees, non-parametric regression, Fisher discriminant analysis, Bayesian network modeling, and a fuzzy logic system. Components and tissues preferably screened for include muscle, adventitia, calcium deposits, cholesterol deposits, lipids, fibrous plaque, collagen, and thrombus.

In preferred embodiments, especially those where data from multiple imaging modalities or imaging instruments is used, the data is converted to a common format. It is also preferably computationally brought into registration, often using a landmark, be it one that represents a physical feature (e.g., an arterial branch point such as the carotid bifurcation) or a computational feature, such as a vessel lumen centroid calculated from the data being processed. In some embodiments, a three-dimensional model of the blood vessel over at least a portion of the region bounded by the most distantly spaced cross sections being analyzed can be rendered computationally. A plurality of other analyses or operations may also be performed, including calculation of total plaque volume or burden, the location and/or composition of plaque, etc. Depending on the analyses or operations performed, the results of the analysis may be output into one or more output files and/or be transmitted or transferred to a different location in the system for storage. Alternatively, the data may be transmitted to a different location.

Yet another aspect of the invention concerns assessing effectiveness of a therapeutic regimen or determining a therapeutic regimen. Such methods employ the plaque detection and analysis aspect of the invention, in conjunction with delivering or determining a therapeutic regimen, as the case may be, depending on the results of the plaque detection, and preferably classification, analysis. In some embodiments, the therapeutic regimen comprises administration of a drug expected to stabilize or reduce the plaque burden in a patient over time. If desired, the effect of the therapeutic regimen can be assessed by a follow-up analysis, preferably by performing an additional plaque detection, and preferably classification, analysis according to the invention. As will be appreciated, the instant method will be useful not only in delivering approved treatment strategies, but also in developing new strategies. As an example, these methods can be used in assessing clinical efficacy of investigational treatments, including those related to drugs being assessed for treating cardiovascular and/or cerebrovascular disease.

Another aspect of the invention relates to computer program products that comprise a computer usable medium having computer readable program code embodied therein, wherein the computer readable program code is configured to implement an automated method according to the invention on a computer adapted to execute the computer readable program code.

Computational systems configured to execute such computer readable program code represent an additional aspect of the invention, as do business models for implementing such methods, for example, ASP and API business models. For example, in an ASP model, the medical imaging system and computer system configured to execute the computer readable program code of the invention are located at different locations. Frequently, the computer system resides in a computational center physically removed from each of a plurality of imaging centers, each of which comprises a medical imaging system capable of generating raw data from which processable data can be derived. In preferred embodiments, at least one of the imaging centers communicates raw data to the computational center via a telecommunications link.

With regard to computer systems, they typically comprise a computer adapted to execute the computer readable program code of the invention, a data storage system in communication with the computer, and optionally operably connected to the computer a communications interface for receiving data to be processed by, or for sending data after processing by, the computer.

BRIEF DESCRIPTION OF THE FIGURES

These and other aspects and embodiments of the present invention will become evident upon reference to the following detailed description and attached drawings that represent certain preferred embodiments of the invention, which drawings can be summarized as follows:

FIG. 2 has two panels, A and B. Panel A is an image of generated from raw magnetic resonance data (in DICOM format) obtained from a commercial MRI instrument that shows the illumination gradients from surface coils. Panel B represents the same image as shown in Panel A after histogram equalization.

Figure 1:
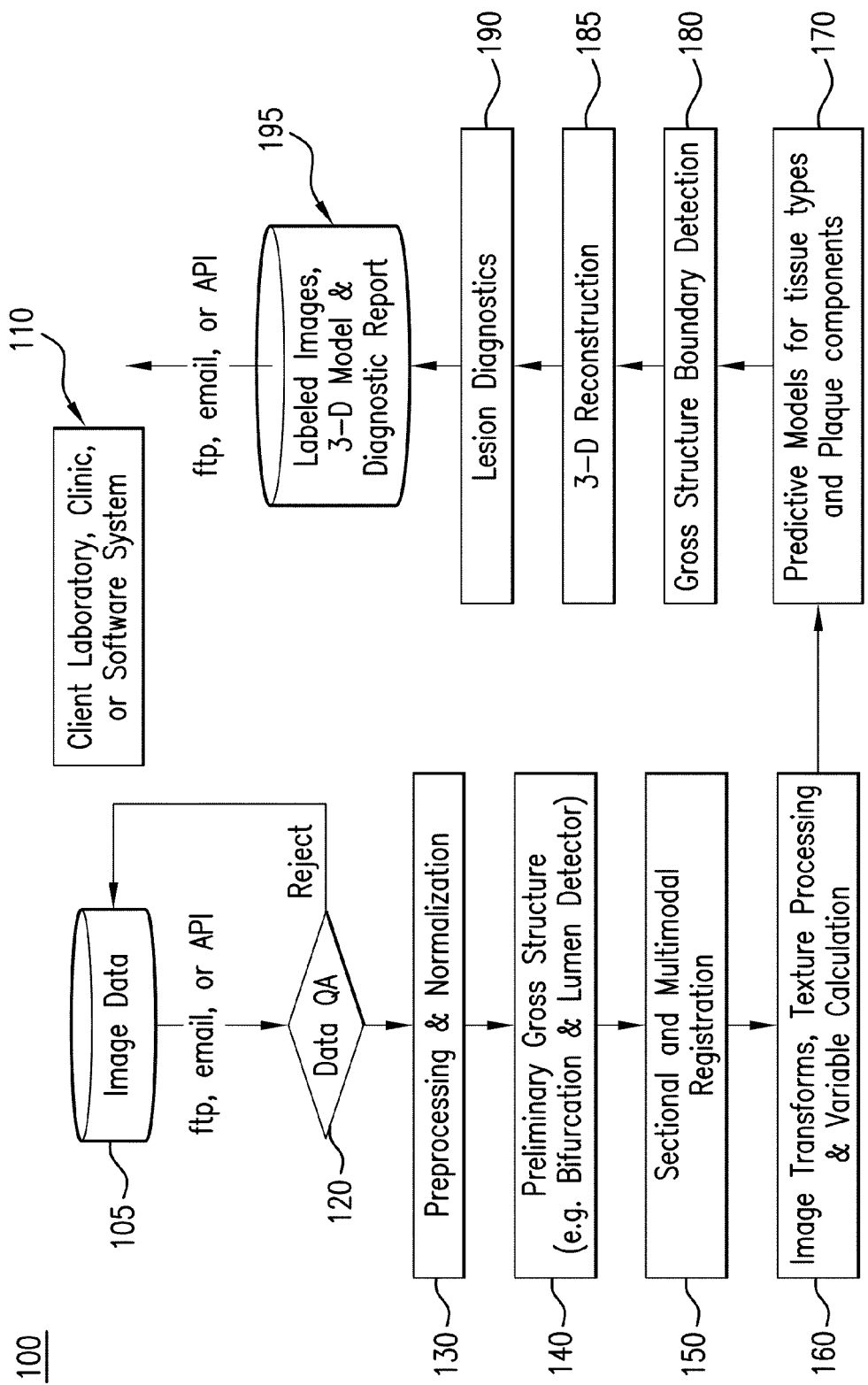
FIG. 1 is a flowchart that shows an overview of several preferred embodiments of the invention.
Figure 3A:
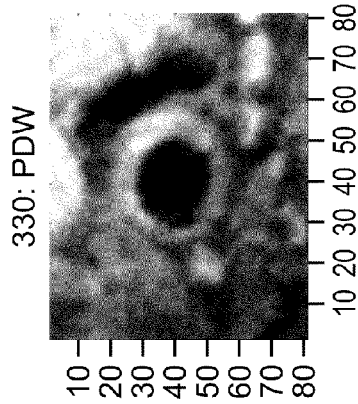
FIG. 3 has four panels, A-D. Panel A shows an MRI image derived from data obtained using a T1-weighted (T1W) modality. Panel B shows an MRI image derived from data obtained using a T2-weighted (T2W) modality. Panel C shows an MRI image derived from data obtained using a PD-weighted (PDW) modality. Panel D shows the results of multimodal registration of the in vivo T1W, T2W, and PDW images.
Figure 3B:
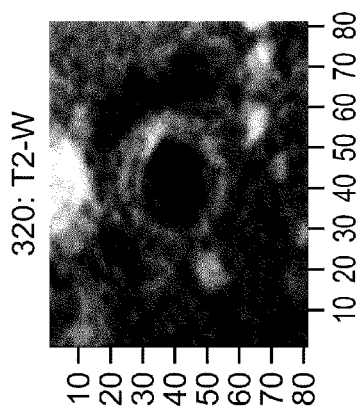
Figure 3C:
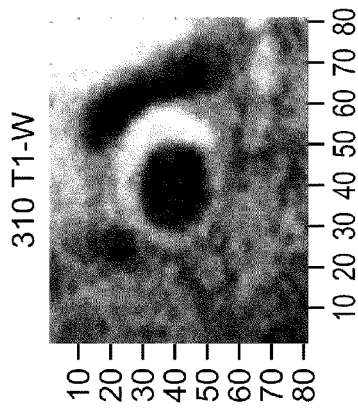
Figure 3D:
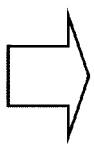
Figure 3D:
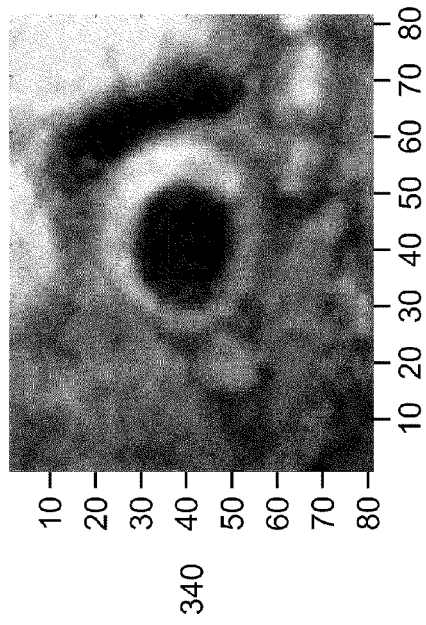

As those in the art will appreciate, the embodiments represented in the attached drawings are representative only and do not depict the actual scope of the invention.

DETAILED DESCRIPTION

Before the present invention is described in detail, it is understood that the invention is not limited to the particular imaging techniques, methodology, and systems described, as these may vary. It is also to be understood that the terminology used herein is for the purpose of describing particular embodiments only, and is not intended to limit the scope of the invention described herein.

The present invention concerns automated, objective methods and systems to detect and analyze plaque in one or more regions of a patient's vasculature. In general, the inventive methods involve a comparison of data derived from one, two, or three-dimensional images obtained using a medical imaging system (or data collection precursors to such systems) to examine a patient against a database containing information that allows the patient-derived data to be classified and plaque detected, if present. Further comparisons allow plaque to be analyzed, for example, classified (e.g., as stable or vulnerable plaque), if desired. Pattern recognition techniques are used to perform these comparisons. This information, alone or in conjunction with other data about the patient, can be used for various purposes, for example, to determine a course of therapy, stratify a patient's risk for suffering a subsequent adverse event (e.g., a stroke or heart attack). Imaging technologies useful in practicing the invention are those that can be used to generate three-dimensional images of blood vessels, and include CAT, PET, MRI, and ultrasound. At present, MRI is preferred.

In practice, data for a patient is obtained by sending the patient to an MRI (or other imaging) center that will put the patient into an imaging device that generates the basic input data needed to perform the subsequent analysis. To implement the invention, no additional hardware would be needed at imaging centers. Once the raw data are collected, in preferred embodiments they are sent (e.g., via the Internet as one or more encrypted electronic data files) to a center for analysis. The data are then automatically processed to form an individualized product by comparing the patient's data patterns to a database using a set of one or more statistical classifiers. An individualized patient product can then be prepared and sent to the requesting physician. In preferred embodiments, the patient product provides a 3-D visualization of the vasculature of the patient's heart, for example, which may, for instance, indicate the locations of both total plaque and the subset of plaque vulnerable to rupture. It may also be useful to quantify the volume of individual plaques, total plaque, individual vulnerable plaques, and total vulnerable plaque. When used over time to produce a plurality of analyses for a given patient, particularly one undergoing treatment for an atherosclerotic disease, the methods and systems of the invention can be used to assess the efficacy of the treatment. For example, has the treatment lessened the patient's overall plaque burden (and/or reduced the rate of progression (or expected progression) of this burden); has the percentage or amount of vulnerable plaque been reduced; has the composition of particular plaques changed over time (e.g., become more or less stable, etc.); etc.?

The methods of the invention can readily be embodied in software, hardware, or a combination of these in order to provide automated, non-invasive, and objective detection and analysis (e.g., plaque identification and classification) of atherosclerotic (AT) lesions in a user-friendly and reproducible manner. The invention allows researchers, physicians, and patients to readily derive increased benefit from existing disease management and/or treatment strategies. These important diagnostic and prognostic methods and systems will thus improve therapy and outcomes with respect to the class of diseases that constitute the single leading cause of morbidity and mortality in the developed world.

1. Automated Methods for Vascular Plaque Detection and Analysis.

In general, the methods of the invention are based on the computational analysis of data for a patient obtained using a medical imaging system to determine whether a patient suffers from atherosclerosis in at least a portion of his/her vasculature. To detect vascular plaque, a computer processes and compares data using statistical classifiers to determine if one or more regions of the blood vessel(s) under analysis contain at least one tissue correlated with (i.e., known to be associated with) the presence of vascular plaque. If desired, plaque, if present, can also be classified, for example as stable or vulnerable plaque, depending on the tissues identified in the region of the plaque. In addition, assessments such as plaque volume, plaque burden, disease progression, treatment efficacy, etc. can also be performed.

Initially, raw image data of least one point, line, plane, cross-section, or three- (or more) dimensional image of a patient's body, particularly all or a portion of a blood vessel, is gathered using a medical imaging system. As used herein, "cross-section" will be understood to mean that the actual data embodied therein may refer to a lesser or greater quantity of data. Preferred medical imaging systems are non-invasive systems, and include MRI instruments. Raw data collected from the imaging instrument is then converted into a form suitable for computer analysis. The analysis is performed using a computer to compare the processed data for a given cross-section with at least one, and preferably several, statistically derived classifiers or predictive models for at least one, and preferably several different, healthy and diseased tissues known to exist in the vasculature. In this way, a model of at least one cross-section of at least one blood vessel can be assembled. When data for several or many cross-sections are obtained, a larger model can be assembled that spans the region defined by the various cross-sections. If desired, the resulting model can be used to reconstruct a three-dimensional model of the region(s) of the blood vessel being analyzed, which model can depict various features of the blood vessel. For example, the three-dimensional model may show the position(s) of plaque inside the vessel. Such models can also be used to calculate a degree of stenosis in one or more regions of a blood vessel, as well as the volume of plaque inside the particular region of the vessel. Plaque volume can be calculated using any suitable approach. For example, the total volume of the blood vessel's lumen in the absence of the plaque could be calculated, as can the volume of the lumen in that region in the presence of the plaque. The difference can be used to represent the estimated volume of plaque in that region, and the degree (e.g., percentage) of stenosis can also be readily calculated. Similarly, plaque burden can be determined, as can other clinical measures of disease.

A. Representative System Configuration.

Using MRI analysis as a representative example, the overall design of a preferred embodiment of a system for plaque detection and analysis according to the invention is schematically illustrated in FIG. 1. As will be appreciated, various components of the system are preferably modular, so that one or more components can be updated or revised without the need for updating or revising the entire system. In addition, many of the steps shown are optional, and have been included in order to describe the currently preferred embodiments of the methods and systems of the invention. Removal of one or more of these optional elements, steps, or processes may be desired in a given application.

As shown in FIG. 1, the process begins with patient MRI data being collected at an MRI center or other facility (110). The raw data (105) collected are passed on to the plaque detection and analysis system either as part of the system resident at the facility where the data were gathered or at a different facility. For rapid data processing at another facility, the data are preferably communicated electronically, for example, as an encrypted data file transmitted over the Internet to a facility containing one or more computers configured to process the data to detect and, if desired, analyze, vascular plaque. Preferably, the raw image data are tested to ensure that it meets minimum quality standards (data quality analysis 120), for example, by calculating a Population Stability Index. If the data are not of sufficient quality (and can not be rendered to sufficient quality in the particular implementation of the invention) to render the output reliable, they are not processed further and a message is preferably transmitted to the imaging center to notice the rejection of the raw image data for analysis. If desired, another copy of the initial raw data can be re-transmitted, or, alternatively, another set of raw data (105) can be collected and re-submitted for analysis.

After satisfying quality assurance parameters, the raw data are approved for further processing. In preferred embodiments, the raw data are pre-processed and/or normalized (step 130) and then computationally analyzed to preliminarily identify gross structures in the blood vessel (140). When two or more modes of data are available for analysis, sections and different data modes are then brought into registration (150) using any suitable algorithm configured for computer-based implementation. Image transformation, texture processing, and variable calculation (i.e., image processing, 160) may then be then performed, after which the data can be classified using statistical classifiers or predictive models to assign tissue classification (170). Gross structure boundaries in the blood vessel can then be determined (step 180), and a three-dimensional reconstruction of the vessel is assembled from the various data (185). Thereafter, lesion (here, vascular plaque) diagnostics are performed, after which a three-dimensional model of the blood vessel can be generated, if desired, along with a diagnostic/prognostic report and/or labeled images (195). If desired, the results are then forwarded to the designated recipient, for example, a physician, clinic, or data storage system for subsequent retrieval.

Several steps of the system described above and illustrated in FIG. 1 are described in greater detail below.

i. Data Input.

Raw image data (105) for a patient can be presented to the plaque assessment system according to the invention through any suitable method. One such preferred method is an ASP (Application Service Provider) model, wherein a patient's raw image data (105) is transmitted from an imaging facility via secure Internet connection. Another model is the (Application Program Interface, or "API") model, wherein the plaque assessment system is embedded within a software package that is installed on-site at the imaging facility.

ii. Image Processing and Formatting.

In preferred embodiments, raw image data are subjected to a quality assurance examination to ensure it satisfies minimum criteria for data quality. Data meeting these standards is then pre-processed. For instance, data received from different MRI imaging facilities may be in different formats, due to the use of different MRI instruments, different versions instrument control software, etc. A preferred common format for MRI-derived data are DICOM, although other formats may be adapted for use in accordance with this invention. Also, because of hardware differences between various MRI instruments and RF coils, resolution and scale can, if desired, be compensated for in a manner that produces data that are relatively free of noise and distortion.

As is known, MRI signal intensity drops with distance from the surface RF coils ($1/R^2$). As a result, images developed from raw MRI data exhibit an "illumination gradient", as shown in FIG. 2. If desired, any now-known or later-developed algorithm useful in correcting for this effect can be employed. Suitable methods include histogram equalization (Gonzalas and Woods, *Digital Image Processing*, 1992 Addison Wesley), as well as using wavelets to model RF coil function. Other algorithms that can be used to correct this effect are available as part of commercial image processing software tools such as MATLAB (Mathworks, Inc., Natick, Mass.). See also Han, et al. (2001), *J. Mag. Res. Imaging*, vol. 13:428-436.

Robust image discrimination rarely depends on absolute (rather than relative) pixel intensity, primarily because intensity often depends on the particular conditions and imaging machine used to collect the data. Consequently, it is usually valuable to normalize the data to their highest pixel intensity in each respective image. Typically, data from each data collection modality (e.g., T1, T2, PDW, TOF, etc.) is normalized independently so that the data for each modality has the same dynamic range. However, additional variables, comparing absolute intramodal intensity differences, may be created using non-normalized data. Multimodal variables, such as the ratio of T1 and T2, for example, measure the ratio of normalized quantities.

The dynamic range of pixel intensities has been observed to contract in some instances, for example, with some in vivo carotid images. By the end of the sequence (closest to the head), the observed resolution can be quite poor, probably as a result of using a localized neck coil. However, depending on application, for example, estimation of overall plaque burden as opposed to plaque classification or the identification of microstructures (such as neovascularization or fibrous cap thickness), low resolution images may still be useful. In addition, blood suppression pulse sequences can also enhance resolution (Yang, et al. (2003), *International J. of Cardiovascular Imaging*, vol. 19:419-428), as can collection of data using several modalities. For example, the fibrous cap of vascular plaque can be distinguished well in TOF images.

iii. Preliminary Gross Structure Identification.

In order to detect and analyze vascular plaque in an imaged cross section of a patient's body, it is often desirable to identify the blood vessel(s) sought to be analyzed. Gross tissue identification allows a region of interest, e.g., a blood vessel, to be extracted for analysis from an MRI slice. This can be readily accomplished using morphological techniques to identify the lumen of the vessel, for example. Of course, identification of other gross morphological features, e.g., arterial muscle, adventitia, etc. can also be employed, alone or in conjunction with lumen detection. When lumen detection is employed, once the initial lumen location has been determined, succeeding image slices can use the estimate of the position of the lumen in the preceding slice to make an initial estimate of the location of the lumen. Once detected, the center of the lumen (i.e., the centroid of the lumen) is preferably re-estimated iteratively for each slice. To avoid the compounding of centroid estimation errors in successive slices, particularly in the context of diseased tissue having irregular features, additional heuristic algorithms, such as re-registration at a more distal axial position and interpolation between slices, can be employed.

iv. Image Registration.

The time intervals required to conduct multimodal MRI scans may introduce inter- and intra-modal alignment and registration errors, due to patient motion, heartbeat, breathing, arterial dilation, etc. For carotid imaging, a plurality of image slices, for example, 12-20 are preferably taken in parallel per scan, which takes 3-4 minutes in current conventional, commercial MRI instruments. Additional scans are required for multimodal images. Hence, the entire process may (at present) take 3-20 or more minutes for carotid imaging using conventional MRI instruments. While gating to heartbeat or respiratory cycle does not yield much benefit on carotid imaging, longer scan times (for example, as may be required for conducting scans using multiple modalities) may increase the potential for a patient to move during the scanning procedure. For coronary artery imaging, because of the motion of a beating heart, gating may be based on EKG to collect the raw magnetic resonance data, although doing so often significantly slows the process per modality, with times of about 10 minutes/modality not being uncommon.

When multiple modalities are employed, inter-modal registration or alignment will most likely be required. Reasonable registration can be attained using a straightforward alignment of the lumen centroids. However, due to the high contrast of blood in all MRI modalities, it is rather trivial to create a "lumen detector" to center images on an important reference point, or landmark. Detecting the lumen allows location of the gross lumen boundary, which can then be used as the starting reference point for image registration. Woods, et al. (1998), *Journal of Computer Assisted Tomography*, vol. 22:139-152. While satisfactory alignment can be achieved through rigid body translation and rotation (see FIG. 3), other more complex methods that consider tissue deformation due, for example, to changes in blood pressure, can also be employed. See, e.g., Dhawan, A. (2003), Medical Image Analysis, IEEE Press Series in Biomedical Engineering.

As will be appreciated, methods that involve more refined alignment, e.g., pixel alignment, preferably employ a metric by which the quality of the registration can be quantified. Such metrics can be as a simple as normalized cross-correlation, or they can be more complex, such as the maximization of mutual information. Viola and Wells (1995), *Alignment by Maximization of Mutual Information*, International Conference on Computer Vision; Wells, et al. (1996), *Med Image Anal.*, vol. 1(1):35-51. It is important to note that when aligning images or data sets developed using different imaging modalities, the reference image and the image to be aligned frequently display differing characteristics. As such, alignment maximization criteria may not exhibit as clear a peak as would be expected if the two images or data sets were collected using the same modality.

For vertical registration, the lumen of the vessel subject to analysis is preferably used align slices from different modalities near a common anatomical reference point, a computerized fiction (e.g., a lumen centroid), or other landmark. Subsequent slices can then readily be aligned from this common point. For example, a convenient reference point in carotid imaging is the carotid bifurcation. Indeed, the analysis described in the examples below used the carotid bifurcation as an axial reference point. Inter-slice intervals in different modalities may also require linear interpolation algorithms.

v. Image Processing.

In preferred embodiments, processable data (i.e., data configured for manipulation by a computer) are passed through image processing algorithms to remove noise as well as to synthesize textural features and other variables of interest. Although non-parametric regression models (e.g., neural networks or Radial Basis Functions) may be used to estimate any arbitrary, non-linear discriminant function. Cybenko, G. (1989), *Mathematical Conti. Signal & Systems*, vol. 2:303-314; Hornik, et al. (1989), *Neural Networks*, vol. 2:359-366; Jang and Sun (1993), *IEEE Trans. Neural Networks*, vol. 4:156-159. As a practical matter, it is useful to incorporate any known relationships into the variable set, to simplify the optimization problem. Common techniques include variable linearization and transforming or combining variables to capture non-linear relationships, and so on. For example, in building a model to discriminate seismic signals, it is overwhelmingly more effective to first transform the time series into the frequency domain. Dowla, et al. (1990), *Bull. Seismo. Soc. Amer.*, vol. 80(5): 1346-1373. The overall objective of image processing, then, is to create transformations of the input image. Types of image processing operations employed fall loosely into several (not mutually-exclusive) classes, based on their mathematical objective: noise reduction; dimension reduction; texture or feature detection; and derived variables (often designed using expert domain knowledge, although they can be defined using mathematical/statistical techniques). Examples of variables and transforms demonstrated to enhance performance of a plaque classification system according to the invention are described in the examples below; however, other image processing techniques known in the art may also be adapted for use in practicing the invention.

vi. Tissue Classification.

After image processing (160), the transformed data are fed into statistical classifiers to classify each pixel in the image as belonging to one of several tissues, including vascular plaque components. Labeling images is a straightforward process of performing a mathematical function on each pixel in the image. One approach for the development of predictive models is described in Example 2, below. A detailed example of building predictive models for plaque classification from MRI images is then provided in Example 3.

vii. Tissue Segmentation.

Figure 12A:
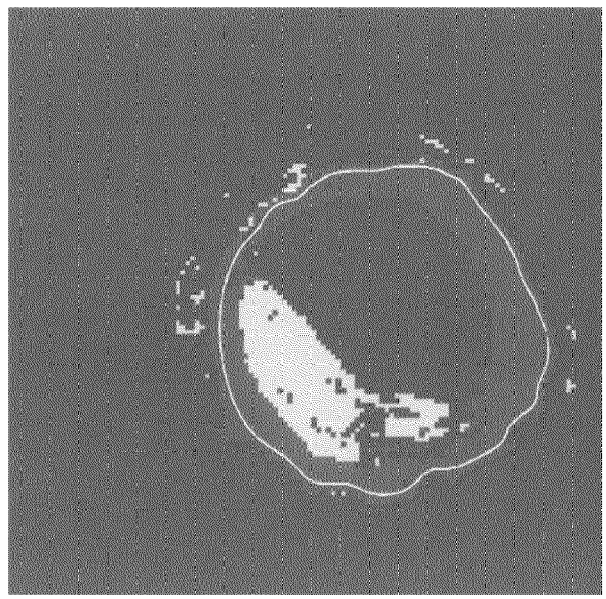
FIG. 12 has two panels, A and B, showing the results of tissue segmentation algorithm performance on two arterial cross sections. Once the tissue segmentation was performed, pixels spuriously labeled as plaque components outside the vessel wall were eliminated, reducing false positives. In addition, plaque burden estimates can be obtained by comparing the ratio of pixels classified as plaque versus the number of pixels within the wall. In these examples, plaque burdens are estimated to be 28% and 62%, respectively.
Figure 12B:
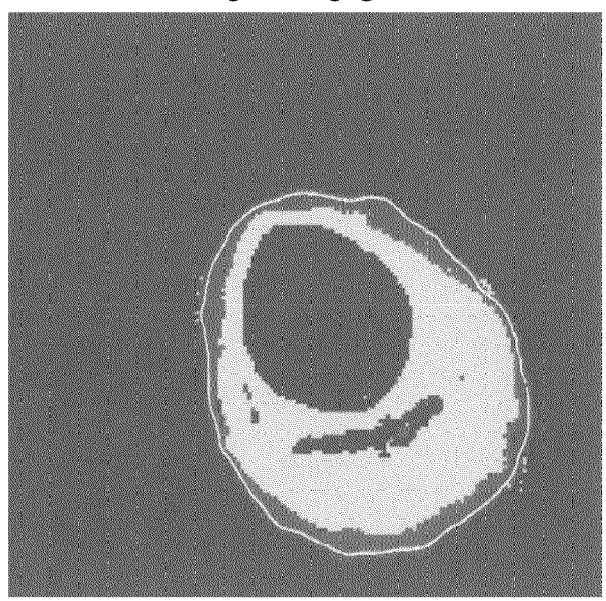

Image segmentation is performed on the output of the tissue classifier in order to highlight tissues of interest, degree of stenosis, etc. as well as to suppress non-relevant features. In many cases, the distinction between plaque components and non-pathological tissues is impossible outside of anatomical context. For example, hard plaque is essentially scar tissue and composed primarily of collagen, as is arterial fascia. Collagen outside the arterial wall is structural, and certainly not pathological. Likewise, lipid or calcium deposits outside the vessel are of no clinical significance in the context of detecting and analyzing plaque inside of blood vessels. Any suitable approach can be used for this process. In a preferred embodiment, domain knowledge can be exploited, as some variables lose sensitivity as a function of radial distance from the lumen boundaries. In another preferred embodiment, excellent results can be achieved using a two-stage approach, whereby tissue type predictions are passed through a second, gross structure processing module. Essentially, the output of the predictive models is fed into image processing algorithms (e.g., gradient-flow and active contour control (Han, et al. (2003), *IEEE Trans. Biomed. Eng.*, vol. 50(6):705-710) to define the boundary of the arterial muscle. All pixels outside this boundary may then removed from consideration as plaque components or other tissues within arterial wall bounding the interior of the blood vessel. An approach using "active contour" algorithm or a "snakes" algorithm (Xu, P. (1997), *Gradient Vector Flow: A New External Force for Snakes*, IEEE Conference on Computer Visual Pattern Recognition; Xu, P. (1997), *Snakes Shapes and Gradient Vector Flow*, IEEE Transactions on Image Processing) is illustrated on the ex vivo data shown in FIG. 12.

Figure 11B:
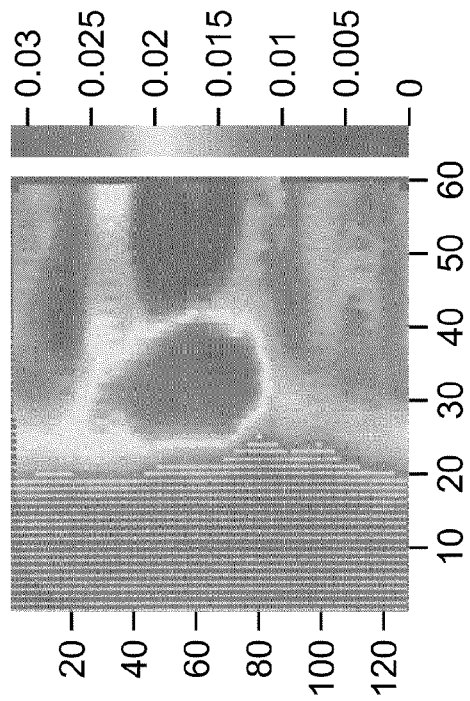
FIG. 11 has two panels, A and B, showing a lumen-centered transformation of the image in Panel A into polar coordinates in Panel B. This transform was used to improve the performance of the gross boundary detection algorithm.
Figure 11A:
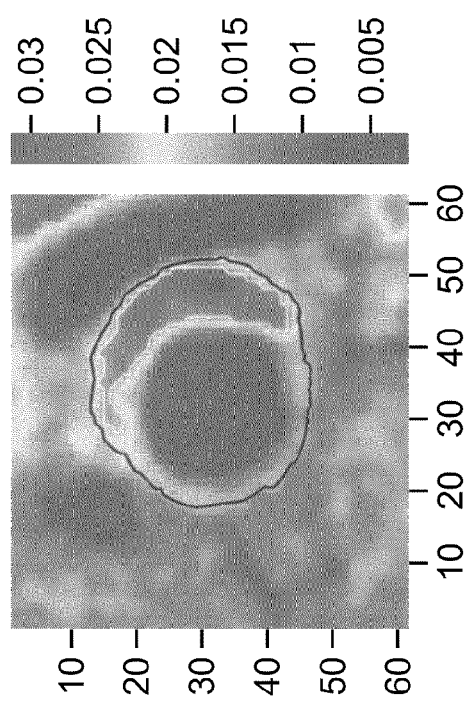

Other segmentation algorithms known to those skilled in the art may also be adapted for use in the context of the invention. For example, tissue segmentation can be accomplished using rules-based methods. The results shown in FIGS. 11 and 13 were obtained using such an approach. Such methods can also be used in connection with boundary detection methods that involve searches for minimum-cost paths (Bishop, C. (1995), *Neural Networks and Statistical Pattern Recognition*, Oxford University Press). In the process used to generate the results shown in FIG. 11, a rules-based method was used to transform vessel images, centered on the lumen, to a radial coordinate system that linearized features that are inherently radial.

viii. Three Dimensional Reconstruction.

Once all slices of an MRI scan have been labeled, a full, three-dimensional model of the artery and plaque can be produced, if desired. Algorithms that detect gross structure (e.g., lumen and exterior arterial wall) directly from DICOM format data obtained from a commercial MRI instrument (for example, an MRI instrument manufactured by General Electric) can be used for this purpose. Example 4 describes a representative example of how such models can be generated.

ix. Lesion Diagnostics.

Lesion diagnostics, including overall size and degree of stenosis, lipid content, plaque size and volume, thrombus, calcification, and so forth, can be estimated from three-dimensional reconstructions of the blood vessel (Voxels). Of course, imaging modalities that selectively detect a plaque component (for example, lipid) can be employed to generate useful models from less data, in that fewer imaging modalities (e.g., T1, T2, PDW, TOF, etc. in the context of MRI analysis) may be required to generate models from which vascular plaque can be detected and analyzed (e.g., classified in terms vulnerability to rupture, etc.).

x. Data Output.

The output of the system can be presented in standardized as well as custom formats to contain such information as may be requested or needed to review the results generated. In some embodiments, the output will consist of the original data, the data labeled by the predictive models, a three-dimensional model, and a diagnostic report, including risk factors and recommended therapies, if indicated. Preferably, the output will be made available directly to the system, particularly in systems based on an API model. In the context of an ASP model, the computer system that performs the analysis will transmit the output file, automatically or upon receipt of an appropriate command, to a specified address. Such an address may be an address for an e-mail account of an attending physician, radiologist, and/or specialist, the patient under examination, the medical imaging facility from which the patient's data were initially transmitted, etc.

xi. Generalization and Standardization.

As will be appreciated, the automated nature of the methods of the invention will allow for the development of standardized data analysis procedures, formats, etc. Also, much of the subjective nature, and thus variability, of current human expert-based examination of imaging data can be done away with by implementing the methods and systems of the invention.

xii. Other Considerations.

As described herein, MRI can be been used to identify morphological plaque features, such as plaque size and fibrous cap thickness, with high sensitivity and specificity. Furthermore, MRI can discriminate plaque components (e.g., fibrous cap, calcification, lipid content, hemorrhage, etc.) characteristic of vulnerable and stable plaque in all of the major arteries: carotid; coronary; and the aorta. Improvements in imaging protocols have been developed to minimize motion artifacts. Worthley, et al. (2001), *Int'l J. Cardiovascular Imaging*, vol. 17:195-201; Kerwin, et al. (2002), *Magnetic Res. In Med.*, vol. 47:1211-1217.

An advantage of MRI is that structures can be imaged using several different modalities. T1-, T2-, PD-, and TOF-weighted images (T1W, T2W, PDW, and TOFW, respectively) of the same anatomical tissue can be quite different, depending on the chemical components and structure of the tissue. For example, calcification, fibrous tissue, and intra-plaque hemorrhages can be distinguished using T2-weighted images. Calcium is very hypointense in Proton Density Weighted (PDW) images, while smooth muscle can be characterized well by a relatively short T. Time-Of-Flight (TOF) weighted images yield good discrimination of intra-plaque hemorrhage and lipid-rich, necrotic cores. Contrast agents can be used to improve the detection of neovasculature, another indicator of plaque vulnerability. Further, other agents, such as labeled antibodies, vesicles containing targeting moieties specific for a component of plaque, can also be used to enhance or add to data collected from a medical imaging system for analysis according to the invention.

The inventors have determined that, at present, plaque detection and analysis according to the instant automated methods based on MRI imaging preferably uses data derived from two, three, or four different imaging modes (e.g., T1, T2, PDW, and TOF) or their derivatives (e.g., T1/T2 ratios) in order to discriminate plaque components from other tissue of a blood vessel, although single and other multi-modal analyses are also within the scope of the invention. Integration of information obtained from multiple contrasts would facilitate even more rapid, accurate, and reproducible assessments of plaque presence, location, and composition. Such analyses can then be used to reduce the number of modalities necessary to measure and classify plaque and possibly lead to design of RF sequences with higher discriminatory power. Similarly, the use of data collection modes specific for particular components of vascular plaque will decrease initial data collection times, as will improvements in imaging equipment hardware, operating software, etc.

2. Applications.

Acute thrombus formation on disrupted/eroded human atherosclerotic lesions plays a critical role on the onset of acute coronary syndromes and progression of atherosclerosis. Pathological evidence has clearly established that it is plaque composition rather than stenotic severity that modulates plaque vulnerability and thrombogenicity. As will be appreciated, the instant methods and systems can be deployed for automated image analysis based on pattern recognition for detecting, measuring, and classifying atherosclerotic plaques in vivo, as well as total plaque burden and related measures. In preferred embodiments, three-dimensional images are derived using MRI. Automation allows fast, objective (observer-independent) data analysis. Such methods will have a variety of applications, including detecting and, if desired, analyzing vascular plaque. Analysis can include, for example, quantitating plaque volume, determining plaque location, and/or assessing plaque composition. Furthermore, the analysis of vascular plaque can focus on one or more regions in vasculature within and/or leading to one or more regions or organs (e.g., brain, heart, kidney, etc.) in patients with or without known cardiovascular disease (which information can help to guide treatment, including surgical intervention and drug therapy), assessing total plaque burden (for example, in the context of patient screening, disease management, etc.), and risk assessment and stratification. These methods can also be used as standard, objective diagnostic and prognostic measures, thereby allowing for comparison of results between laboratories, throughout longitudinal studies, etc. to assess surrogate end points in clinical trials of drugs and other treatments, and across different imaging equipment. In a clinical setting, these methods will also greatly reduce the diagnostic costs involved in measuring the degree of stenosis and detecting thrombosis-prone plaques and reduce the risks to and burdens on patients who might otherwise have to be subjected to more invasive diagnostic methods, while at the same time providing much more useful information than can be obtained using existing methods.

A. Cardiovascular Disease.

Thus, one context in which the invention has application concerns cardiovascular disease. As is known, cardiovascular disease is the single leading cause of death in both men and women. About one-half of individuals in developed nations die of cardiovascular disease, and many more will suffer complications associated with cardiovascular disease and the accompanying lower quality of life. In the U.S. alone, over $15 billion is spent annually on products that visualize the heart and plaque. Recent findings show that vulnerable, not stable, plaque ruptures to cause heart attacks and strokes. Significantly, about 70% of plaque that ruptures to produce heart attacks comes from areas of the vasculature where there is little plaque. To date, however, no objective, rapid method has been developed to distinguish between vulnerable, unstable plaque that is likely to rupture and cause a thrombosis that can lead to a heart attack or stroke, and stable plaque. The instant invention addresses this significant unmet need by providing non-invasive, objective, and rapid methods to detect and analyze plaque throughout the vascular system, particularly in the vasculature of the brain, neck, and heart.

i. Pre-Operative Lesion Diagnostics and Patient Screening.

All current American Heart Association guidelines are based on degree of stenosis and symptom status, without reference to plaque composition. Clearly, more precise pre-surgical diagnostics (for example, plaque composition, e.g., calcification, lipid content, thrombosis, fibrous cap thickness, and so on) will significantly improve the pre-surgical risk estimates, allowing clinicians to more reliably assess the relative risk of surgery over pharmaceutical intervention.

ii. Treatment.

Many cardiovascular and cerebrovascular preventive measures and treatments are assigned to patients based on an estimation of the patient's cardiovascular disease (CVD) or cerebrovascular risk. For purposes of this description, CVD will be discussed as the representative example of atherosclerotic diseases to which the invention in general relates. Thus, the Joint National Committee's hypertension guidelines, and the Adult Treatment Panel's/National Cholesterol Education Panel's cholesterol guidelines define eligibility for treatment by expected CVD risk: that is, they define treatment threshold percentages, or levels of blood pressure or cholesterol at which treatment is initiated, based on CVD risk estimates. Additionally, they define goals of treatment (treatment targets) by expected CVD risk: that is, aggressiveness of treatment, or levels of blood pressure or cholesterol down to which treatment should be advanced.

This is theoretically justified because persons at higher CVD risk have more risk to reduce: the same fractional reduction in risk leads to a larger absolute reduction in risk in those at higher baseline CVD risk, with the greater CVD risk reduction providing greater cost effectiveness of treatment (fewer needed to treat to prevent a CVD event or death); and greater likelihood that the (greater absolute) benefits of treatment will exceed treatment harms.

Current approaches to CVD risk estimation (on which treatment thresholds and targets are predicated) do not incorporate information related to vulnerable plaque. Since vulnerable plaque is a key determinant of CVD risk (arguably the most important determinant), and since this invention allows vulnerable plaque to be detected and analyzed in an objective, automated, and accessible, the accuracy of CVD risk predictions (and risk predictions targeted to different end-organs) can be greatly improved, permitting markedly improved targeting of treatments.

The improved CVD risk prediction (and risk stratification) from effective assessment of, for example, vulnerable plaque, total plaque burden, etc., may have important cost-saving and life-saving implications. Improved targeting of treatments to those truly at risk will save lives for the same cost, and save money for the same savings of life.

Plaque detection and characterization will also permit better decisions regarding who merits medical treatment, and what medical treatments will best serve a particular patient. This may include allocation of (costly) statin cholesterol-lowering drugs (e.g., atorvastatin, simvastatin, pravastatin, lovastatin, rosuvastatin, and fluvastatin), which currently account for the greatest expenditures for any prescription medication in the world, with a $20 billion dollar annual market, and whose usage is expected rise markedly with aging populations. More generally, plaque detection and analysis can also improve treatment decisions for treatment regimens that attack cardiovascular risk through any of a suite of mechanisms, including lowering blood pressure (such as thiazide diuretics, e.g., hydrochlorothiazide, beta blockers such as atenolol, angiotensin converting enzyme inhibitors such as fosinopril, angiotensin receptor blockers such as irbesartan, calcium channel blockers such as nifedipine (diltiazem and verapamil), alpha blockers such as prazocin (terazocin), and vasodilators such hydralazine), stabilizing plaque (as can be achieved by some statins), reducing lipids (as can accomplished using statins; fibric acid derivatives like gemfibrozil or fenofibrate; niacin or variants like niaspan; bile acid sequestrants like colestipol or cholestyramine; or blockers of cholesterol absorption like ezetimibe), reducing inflammation, and/or serving antiplatelet (e.g., aspirin, clopidogrel, etc.) or antithrombotic effects (e.g., tissue plasminogen activator or streptokinase), among others. Of course, depending on the particular patient and condition to be treated, it may be desirable to combine one or more of the foregoing therapies, alone or in combination with other treatments.

The improvements in targeting surgical treatments to those at greatest need may be even more important, since the potential costs and risks associated with surgery should be borne only by those for whom the true risks of the problem exceed the risks of the surgery. Vulnerable plaque assessment may greatly improve determination of whether a patient truly has this level of risk.

iii. Drug Development.

Researchers have used manual evaluation of non-invasive patient image data to monitor the efficacy of cholesterol-lowering drugs in longitudinal studies. However, manual examination is too expensive for general clinical diagnostics. In contrast, the automated methods and systems of the invention can be used to rapidly generate a statistically reliable estimates of plaque composition (e.g., calcification, lipid content, thrombosis, fibrous cap thickness, and so on), total plaque burden, vulnerable plaque burden, the ratio of vulnerable to stable plaque, or lipid deposits, to be used as a surrogates of clinical outcomes (e.g., rupture, stroke, MI), greatly reducing the time and cost of research. Another major advantage afforded by the invention is to significantly reduce the number of patients and the length of follow-up required to demonstrate the effectiveness of cardiovascular and cerebrovascular drugs, including those undergoing clinical trials. For instance, given the significant clinical benefits associated to the use of statins, it might be unethical to perform any new trials that include a placebo. Therefore, to demonstrate a significant advantage over currently used cardiovascular drugs, trials may require at least a few thousands patients and 3-5 years of follow-up.

iv. Enhanced Diagnostics.

Another application for the instant methods and systems concerns provision of superior diagnostic and prognostic tools to patients and physicians. In this regard, plaque detection and analytical data and results derived from use of this invention can be combined with data from other sources to provide even more advanced diagnostic products and services. For example, the Framingham Heart Study database has been used extensively to create scorecards to estimate the risk of cardiovascular disease (CVD). This landmark dataset was developed from tracking 5,209 subjects over time, and from whom a host of predictor variables have been obtained, including age, gender, measures of cholesterol and hypertension, demographic factors, medications, diabetes status, alcohol consumption, smoking history, history of cardiac events (e.g., myocardial infarction (MI), angina pectoris, tachycardia, and bradycardia), revascularization, coronary artery bypass graft procedures, stroke, levels of analytes in the blood (e.g., creatinine, protein), classification of personality (e.g., type A), and a number of "emerging" risk factors, including levels of C-reactive protein, VCAM, ICAM adhesion molecules, and others in the blood. Outcomes accessed include death (cause-specific), and cardiovascular events, including MI, stroke, and sudden death.

There are no MR scans in the Framingham dataset; however, in vivo patient MRI from more recent longitudinal statin drug trials contains both MRI images and pertinent patient histories and risk factors (e.g., blood pressure, cholesterol levels, etc.) is available. For example, a research team at Mt. Sinai collected MR images at six-month intervals over two years (Woods, et al. (1998), *Journal of Computer Assisted Tomography*, vol. 22:139-152). By combining the results obtained from using the instant methods with one or more other data points correlated with CVD, improved even better diagnostic procedures can be implemented.

B. Stroke.

Better knowledge of the composition of atherosclerotic lesions will also allow for more accurate patient risk stratification for stroke, facilitating the selection of appropriate therapies. Approximately 25% of strokes are related to occlusive disease of the cervical internal carotid artery. Treatment options include anti-platelet therapy, endarterectomies, stenting, and angioplasty. Of these treatments, carotid endarterectomy (proactive surgical removal) is the preferred treatment option for advanced carotid lesions, with over 120,000 of these surgeries being performed every year in the United States. Several large clinical studies, including the North American Symptomatic Carotid Endarterectomy Trial (NASCET), the Asymptomatic Carotid Atherosclerosis Study (ACAS), and the European Carotid Surgery Trial group (ECST), have shown this procedure to significantly reduce the risk of stroke under certain limitations. For symptomatic patients with 70% stenosis, the overall reduction in two-year risk of stroke has been estimated to be 17%. Surgery also increases the risk of perioperative events; mortality increases from 0.3% to 0.6% in surgery patients; major stroke increases from 3.3% to 5.5%; and cerebrovascular events increase from 3.3% to 5.5%. For asymptomatic patients with greater than 60% stenosis, the aggregate risk of stroke and perioperative stroke or death is estimated to be 5.1% for surgical patients, compared to 11% for those treated medically. Moreover, evidence suggests that adverse outcome estimates derived from trials underestimate the likelihood of adverse outcomes in real world application—further increasing the importance of identifying those for whom true benefit is likely.

Use of the instant methods will allow patients to be better assessed so that the appropriate therapy can be implemented. Also, as with cardiovascular disease, screening will allow patients to be diagnosed much earlier in the development of disease, enabling early therapeutic intervention and much greater risk reduction over time.

3. Computer-Based Implementations.

The various techniques, methods, and aspects of the invention described above can be implemented in part or in whole using computer-based systems and methods. Additionally, computer-based systems and methods can be used to augment or enhance the functionality described above, increase the speed at which the functions can be performed, and provide additional features and aspects as a part of or in addition to those of the present invention described elsewhere in this document. Various computer-based systems, methods and implementations in accordance with the above-described technology are now presented.

The various embodiments, aspects, and features of the invention described above may be implemented using hardware, software, or a combination thereof and may be implemented using a computing system having one or more processors. In fact, in one embodiment, these elements are implemented using a processor-based system capable of carrying out the functionality described with respect thereto. An example processor-based system includes one or more processors. Each processor is connected to a communication bus. Various software embodiments are described in terms of this example computer system. The embodiments, features, and functionality of the invention in this specification are not dependent on a particular computer system or processor architecture or on a particular operating system. In fact, given the instant description, it will be apparent to a person of ordinary skill in the relevant art how to implement the invention using other computer or processor systems and/or architectures.

The various techniques, methods, and aspects of the invention described above can be implemented in part or in whole using computer-based systems and methods. Additionally, computer-based systems and methods can be used to augment or enhance the functionality described above, increase the speed at which the functions can be performed, and provide additional features and aspects as a part of or in addition to those of the present invention described elsewhere in this document. Various computer-based systems, methods and implementations in accordance with the above-described technology are now presented.

The various embodiments, aspects, and features of the invention described above may be implemented using hardware, software, or a combination thereof and may be implemented using a computing system having one or more processors. In fact, in one embodiment, these elements are implemented using a processor-based system capable of carrying out the functionality described with respect thereto. An example processor-based system includes one or more processors. Each processor is connected to a communication bus. Various software embodiments are described in terms of this example computer system. The embodiments, features, and functionality of the invention in this specification are not dependent on a particular computer system or processor architecture or on a particular operating system. In fact, given the instant description, it will be apparent to a person of ordinary skill in the relevant art how to implement the invention using other computer or processor systems and/or architectures.

In general, a processor-based system may include a main memory, preferably random access memory (RAM), and can also include one or more other secondary memories, including disk drives, tape drives, removable storage drives (e.g., pluggable or removable memory devices and tape drives, CD-ROM drives, DVD drives, floppy disk drives, optical disk drives, etc.). In alternative embodiments, secondary memories include other data storage devices for allowing computer programs or other instructions to be called or otherwise loaded into the computer system.

A computer system of the invention can also include a communications interface (preferably compatible with a telecommunications network) to allow software and data to be transferred to, from, or between the computer system and one or more external devices. Examples of communications interfaces include modems, a network interface (such as, for example, an Ethernet card), a communications port, a PCMCIA slot and card, etc. Software and data transferred via communications interface will be in the form of signals that can be electronic, electromagnetic, optical, or other signals capable of being received by the communications interface. These signals are usually provided to communications interface via a channel that carries signals and can be implemented using a wireless medium, wire, cable, fiber optics, or other communications medium. Some examples of a channel include a phone line, a cellular phone link, an RF link, a network interface, and other communications channels.

In this document, the terms "computer program product" and the like generally refer to media such as removable storage device, a disk capable of installation in disk drive, and signals on channel. These computer program products provide software or program instructions to the computer processor(s). Computer programs (also called computer control logic) are usually stored in a main memory and/or secondary memory. Computer programs can also be received via a communications interface. Computer programs, when executed, enable the computer system to perform the features of the present invention as described herein. In particular, the computer programs, when executed, enable the processor(s) to perform the features of the present invention. Accordingly, computer programs represent controllers of the computer system.

In embodiments where the invention is implemented using software, the software may be stored in, or transmitted via, a computer program product and loaded into computer system using any suitable device or communications interface. The control logic (software), when executed by the processor(s), causes the processor to perform the functions of the invention as described herein. In other embodiment, the methods of the invention implemented primarily in hardware, or a combination of hardware and software, using, for example, hardware components such as PALs, application specific integrated circuits (ASICs), or other hardware components. Implementation of a hardware state machine so as to perform the functions described herein will be apparent to persons skilled in the relevant art(s).

EXAMPLES

The following Examples are provided to illustrate certain aspects of the present invention and to aid those of skill in the art in practicing the invention. These Examples are in no way to be considered to limit the scope of the invention in any manner.

Example 1

Image Processing

This example describes several particularly preferred techniques for processing image data in the context of this invention, including noise reduction, dimension reduction, and texture processing.

A. Noise Reduction.

Composite multi-contrast images were processed in order to reduce noise and introduce smoothing. In each case, the image was first median-filtered to remove noise with impulse characteristics, then smoothed with an adaptive Wiener filter that adjusts to statistics in the surrounding 'N' pixel neighborhood. The mean and variance are estimated from the intensities 'a' at pixel locations $n_1$, $n_2$:

$$\mu=(1/N^2)\Sigma a(n_1,n_2); \sigma^2=(1/N^2)\Sigma a^2(n_1,n_2)-\mu^2$$

These estimates are then used to assign the parameter 'b' to a Wiener filter$^j$:

$$b(n_1, n_2) = \mu + \frac{(\sigma^2 + v^2)}{\sigma^2}(a(n_1 + n_2) - \mu^2)$$

A 2-dimensional convolution was performed on each image intensity plane with the coefficients b above.

B. Dimension Reduction.

Because of the number of data points and variables to be processed, in order to minimize the effects of noise, it is preferred to reduce the dimensionality of the dataset to create fewer, but more statistically-significant, variables. Cluster analysis is only one of many methods employed to reduce noise and dimensionality of raw data generated by an imaging instrument to its most salient features. K-Means clustering is one example of a clustering algorithm. In such an algorithm, 'K' classes are formed, the members of which reside in (feature-space) locations that are least distant from the estimated centroid of each class. This approach makes an initial estimation at the cluster centroids and then re-estimates those centroids according to updated class memberships. This method makes an initial estimation at the cluster centroids and then re-estimates those centroids according to updated class memberships.

The steps underlying the K-means clustering algorithm are:
  i. select a number of clusters 'k' with initial centroids;
  ii. partition data points into k clusters by assigning each data point to its closest cluster centroid;
  iii. compute a cluster assignment matrix; and
  iv. estimate the centroids of each cluster.

Figure 7C:
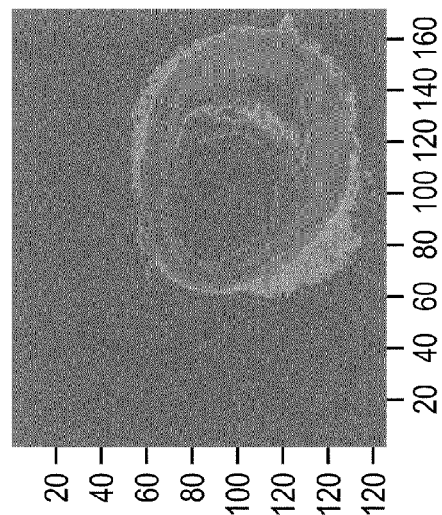
FIG. 7 has three panels, A-C, and shows images processed using a K-means clustering algorithm.
Figure 7B:
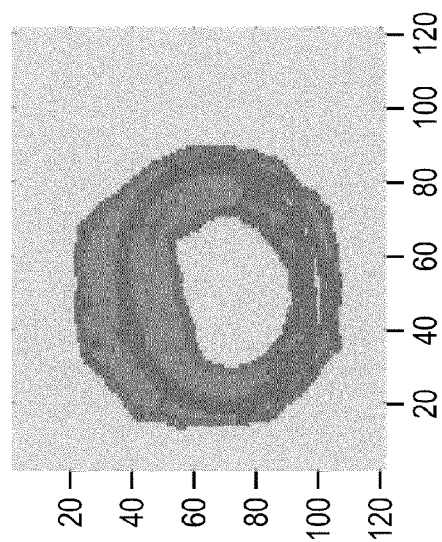
Figure 7A:
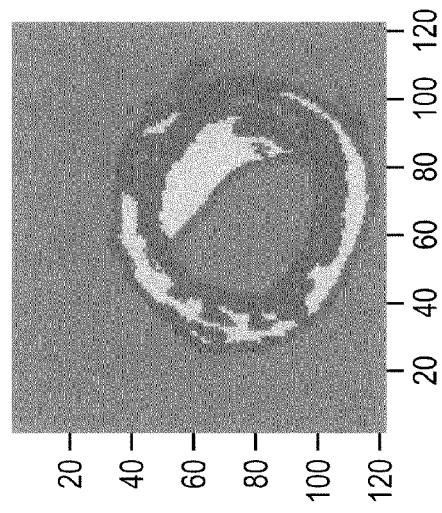

Steps ii-iv are repeated until stopping criteria are reached, typically when the members stop changing cluster membership. See Bishop (1995), Neural Networks and Statistical Pattern Recognition, Oxford University Press. Exemplary cluster analysis results are shown in FIG. 7. From the figure it is clear that some clusters had high correlation to particular tissue types. Texture clustering produced results that were visually quite satisfying, but statistically not as good as a predictive model. The K-means cluster categories were thus used as inputs into the predictive models. Other tools known in the art may also be used to reduce dimensionality, including approaches that combine the theoretical nonlinear curve fitting capability of the typical artificial neural network (ANN) with the stability of hierarchical techniques (Bates White, LLC software, RDMS™). As a result, the estimation routines are exposed only to those inputs that are known to have some predictive power on their own, and that may also embody a number of the most useful underlying nonlinear effects in the model. These steps allow the ANN training stage to focus on a problem with lower dimensionality and with less nonlinearity in the parameters than otherwise required. Still other techniques include Principal Component Analysis, Independent Component Analysis (Bell and Sejnowski (1995), *Neural Computation*, vol. (7)6:1129-1159), and local information metrics (Haralick, R. (1979), *Proc. IEEE*, vol. 67(5)).

C. Texture Measures.

Tissues and plaque components are visually distinguishable by their texture. For example, muscle and collagenous tissues are often striated, while necrotic cores appear mottled. There are no formal mathematical definitions of texture, but these features have mathematical correlates, such as information content, spatial frequencies, and so forth. One commonly used classification distinguishes 28 texture measures. Here, two classes of texture measures, statistics on the local intensity variations and spatial frequency, were used. Statistical pixel measures used were standard statistical quantities, applied to neighborhoods of various sizes. A discrete cosine transform was used to generate an estimate of spatial spectral energy for both 'x' and 'y' orientations. For example, a pixel area that is rich in fine detail has a greater proportion of energy in higher spatial frequencies. The expression for a 2D DCT is:

$$B_{pq} = \alpha_p \alpha_q \sum_{m=0}^{M-1} \sum_{n=0}^{N-1} A_{mn} \cos\frac{\pi(2m+1)p}{2M} \cos\frac{\pi(2n+1)q}{2N}, \begin{Bmatrix} 0 \le p \le M-1 \\ 0 \le q \le N-1 \end{Bmatrix}$$

$$\alpha_p = \begin{Bmatrix} 1/\sqrt{M}, p=0 \\ \sqrt{2/M}, 1 \le p \le M-1 \end{Bmatrix}, \alpha = \begin{Bmatrix} 1/\sqrt{N}, q=0 \\ \sqrt{2/N}, 1 \le q \le N-1 \end{Bmatrix}$$

D. Derived Variables.

Derived variables are synthesized from basic entities purported to have predictive properties. Two variables falling under this category include products and ratios of raw variables and other combinations of the three data types. Three types of derived variables found to have strong discriminatory power include: (i) a "Fat Detector," defined as the ratio T1/T2 that is useful in the detection of lipids; (ii) an axes rotation: YCbCr: In this format, luminance information is stored as a single component (Y), and chrominance information is stored as two color-difference components (Cb, Cr). Cb represents the difference between the blue component and a reference value. Cr represents the difference between the red component and a reference value; and (iii) a local environment variable, based on the geometric distance from the lumen boundary. Examples of other potentially valuable image features are given in Table 1, below.

TABLE 1

Examples of image processing variables and transforms

| Class | Transform |
|---|---|
| Textural Measures | Mean, Variance, Skew, Median, Inter-Quartile Range, Minimum, Maximum, Standard deviation, Range, Kurtosis, Local Information Content |
| Textural Measures | Discrete Cosine Transform, wavelet transforms, orientation |
| Derived Variables | Ratios (e.g., T1/T2), distance from lumen, distance from arterial wall |
| Derived Variables | RGB to YCbCr Color Axes Rotation |
| Dimension Reduction | K-Means Clustering, Principal components, Independent Component analysis |

Example 2

Predictive Model Development

A "model" is a mathematical or statistical representation of data or a system, used to explain or predict behaviors under novel conditions. Models can be mechanistic (commonly employed in the physical sciences and engineering) or empirical/statistical (wherein the model predictions do not purport to explain the underlying causal relationships). Two relevant applications of statistical modeling are to develop statistical classifiers and predictive models. Statistical classifiers are designed to discriminate classes of objects based on a set of observations. Predictive models attempt to predict an outcome or forecast a future value from a current observation or series of observations. This invention employs both types of models: statistical classifiers are used to classify tissue and plaque components; and predictive models are used to predict risks associated with, for example, cardiovascular disease (CVD).

Figure 4:
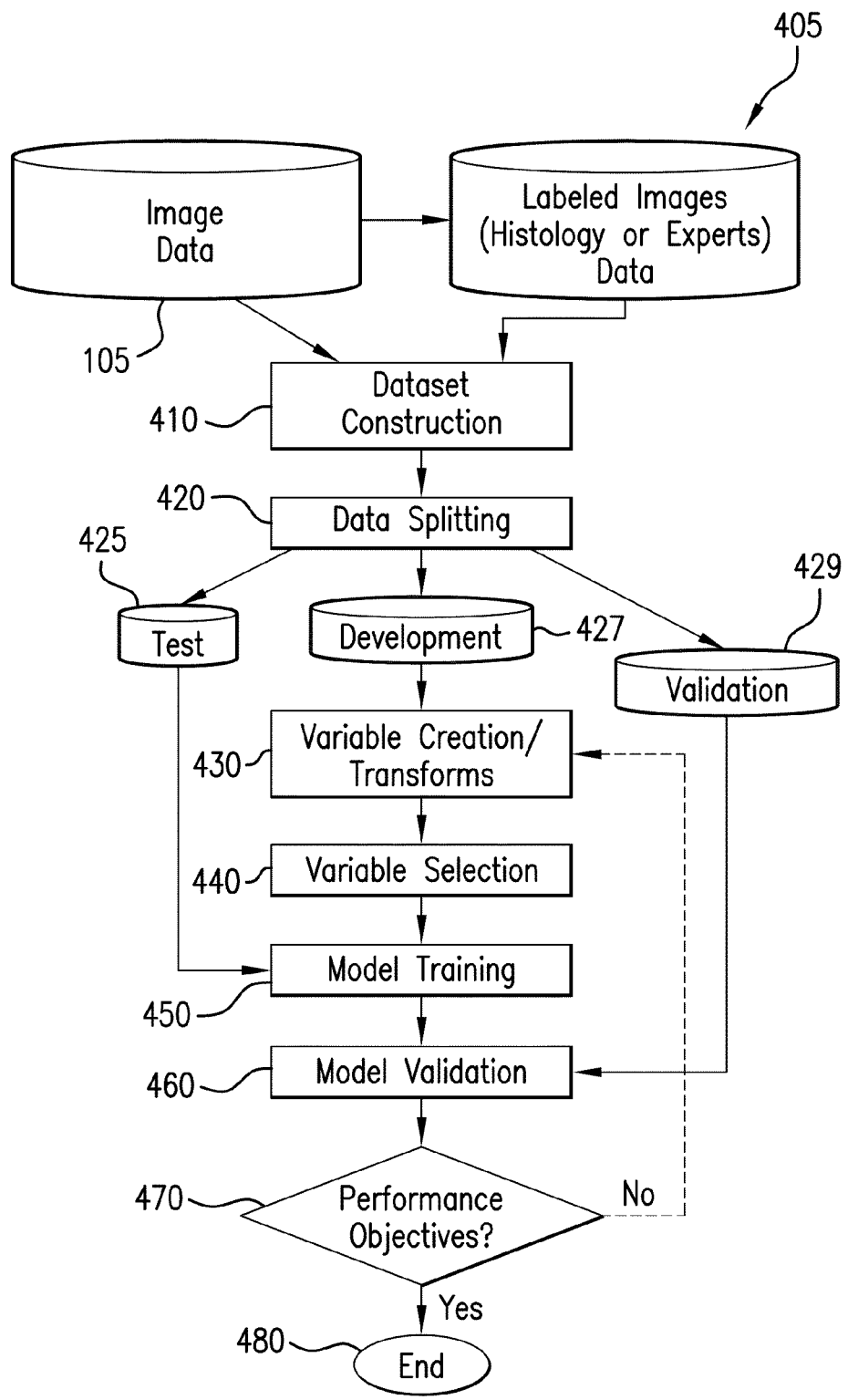
FIG. 4 is a flowchart showing a process for predictive models useful in the context of the invention.

The process of model development depends on the particular application, but some basic procedures, illustrated schematically in FIG. 4, are common to typical model development efforts. First, a modeling dataset must be constructed, including a series of observations ("patterns") and known outcomes, values, or classes corresponding to each observation (referred to as "labeled" or "target" values). In FIG. 4, this is characterized as dataset construction 410. This modeling dataset is used to build (or "train") a predictive model. The model is then used to classify novel (or unlabelled) patterns. Model development is often an iterative process of variable creation, selection, model training, and evaluation, as described below.

A. Dataset Construction.

Figure 5A:
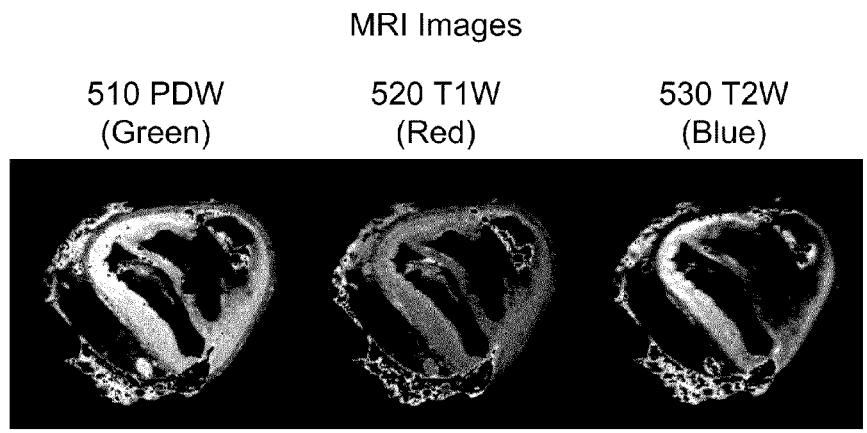
FIG. 5 has four panels, A-D, illustrating the process of data labeling from MRI images. As will be appreciated, image data, including MRI images, can be generated from data collected using different protocols (modalities). In this figure, Panel A shows MRI images of a cross section of a human artery imaged using three standard MRI imaging modalities: proton density weighted (PDW), T1 relaxation time (T1) weighted (T1W), and T2 relaxation time (T2) weighted (T2W). For easy visual interpretation, these PDW, T1W, and T2W images (510, 520, and 530, respectively) can be combined to create a false-color composite MR image 540 (Green=PDW, Red=T1, Blue=T2), shown in Panel B. In the composite image shown in Panel B, multi-contrast normalized grayscale images 510, 520, and 530 were linearly mapped as green, red, and blue channels, respectively, where black was mapped to zero and white was mapped to 255 in each color channel to create a color composite image and render it three-dimensionally using MATLAB. Tissues with similar chemical and environmental properties tend to have similar colors. Additional cues as to tissue type include anatomical location (e.g., inside or outside the muscle wall, i.e., inside or outside the blood vessel) and texture (e.g., muscle tends to be striated, whereas soft plaque typically appears "mottled"). Expert radiologists can often classify fibrous or vulnerable plaque by detailed manual inspection of such data, but such efforts are extremely time consuming and subjective. To develop an automated system for classifying plaque, the model must be "trained" on known examples ("ground truth"). One can train a model to mimic the performance of an expert, but it is preferred to label these images, or the data used to generate images, with the most objective criteria possible, such as validation using histopathology sections of the tissue. Panel C shows the histopathology (ground truth) of the artery cross section used to generate the images shown in Panels A and B. Panel D of FIG. 5 shows a labeled image used for model training, with each tissue class of interest labeled with a different target color. Arterial muscle (media, 565) is pink; adventitia (fascia or collagen, 570) is bright yellow; thrombus (clotted blood, 575) is red; fibrous plaque (580) is pale yellow; lipid (585) is white, and the vessel lumen (590) is black.
Figures 5B, 5C:
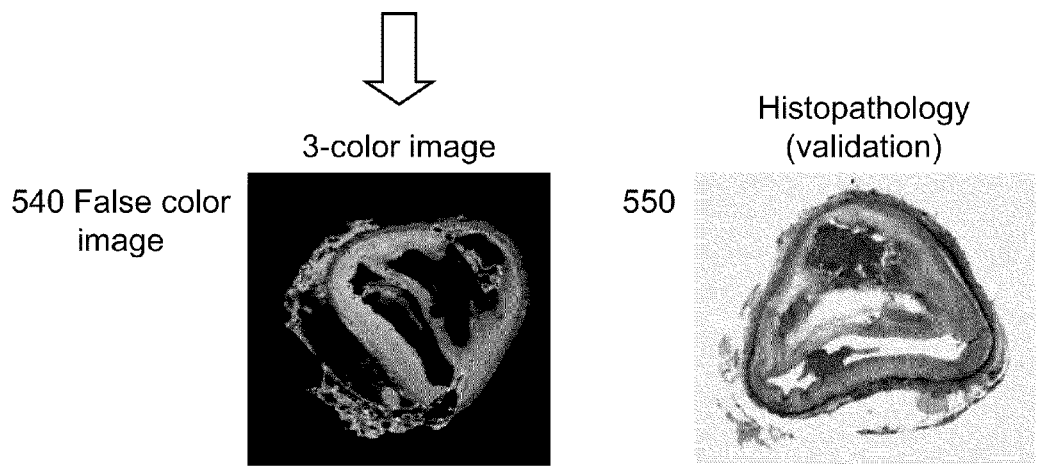
Figure 5D:
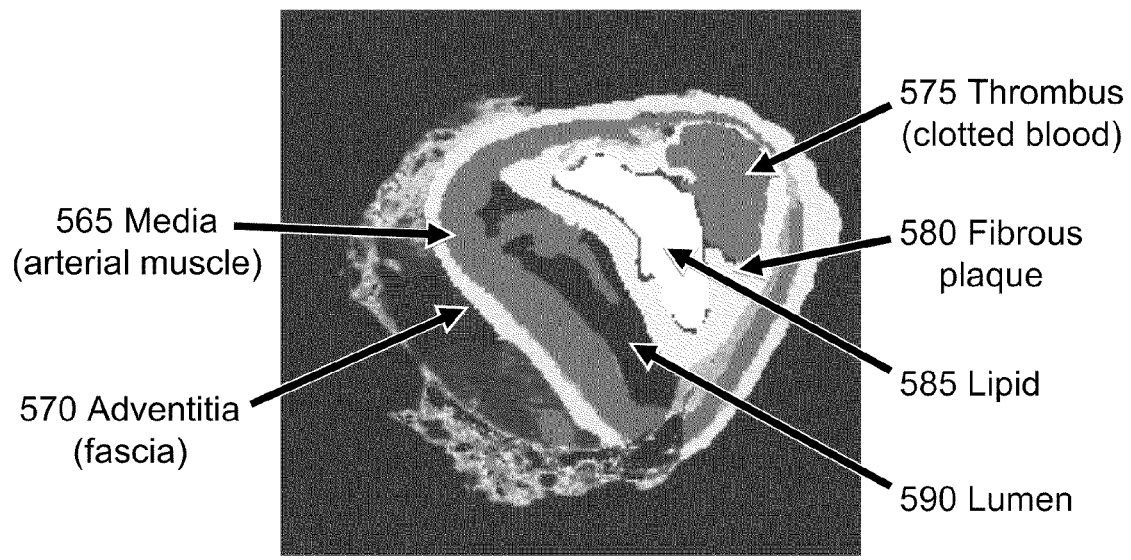
Figure 6A:
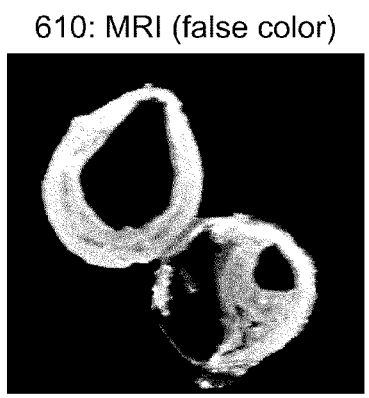
FIG. 6 has three panels, A-C, and presents another example of data labeling. Panel A shows a false color composite MR image (610) of a cross section of two arteries. MR image 610 was generated by combining grayscale MR images generated using three MRI modalities, PDW, T1W, and T2W, as described in connection with the false color image shown in FIG. 5. Panel B shows the histopathology of the artery cross sections. Panel C shows the labeled image (630), labeled analogously to the MR image in Panel D of FIG. 5.
Figure 6B:
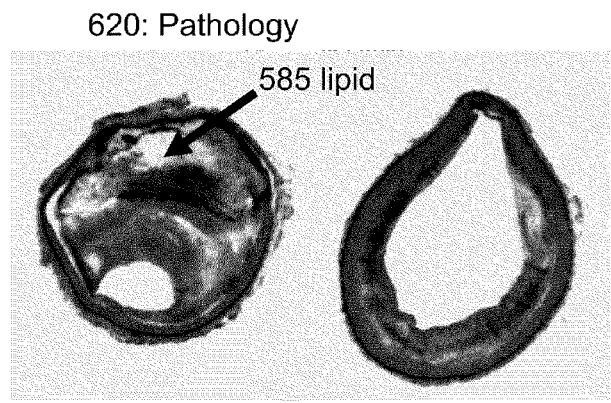
Figure 6C:
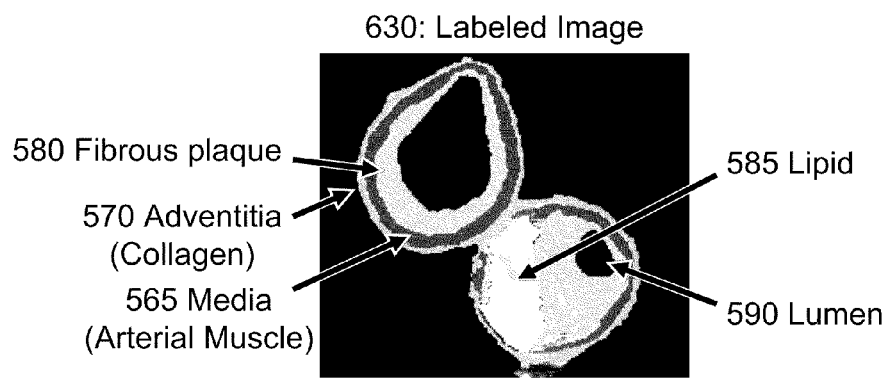

The first step in the model building process is generally to assemble all the available facts, measurements, or other observations that might be relevant to the problem at hand into a dataset. Each record in the dataset corresponds to all the available information on a given event. In order to build a predictive model, "target values" should be established for at least some records in the dataset. In mathematical terms, the target values define the dependent variables. In the example application of CVD risk prediction, targets can be set using observed clinical outcomes data from longitudinal clinical studies. In the context of plaque detection and analysis (e.g., classification), the targets correspond to, as examples, images labeled by a human expert or validated by histological examination. FIG. 5 illustrates the data labeling process used in one such application. In this example, each pattern/target pair is commonly referred to as an exemplar, or training example, which are used to train, test, or validate the model. As will be appreciated, what constitutes a pattern exemplar depends on the modeling objective.

i. Data Splitting.

As illustrated in FIG. 4, the implementation of models typically includes data splitting (step 420). Most model development efforts require at least two, and preferably at least three data partitions, a development data set (data used to build/train the model) 427, a test dataset (data used to evaluate and select individual variables, preliminary models, and so on) 425, and a validation dataset (data to estimate final performance) 429. To serve this purpose, the initial data are randomly split into three datasets, which do not necessarily have equal sizes. For example, the data might be split 50% development (427), 25% test (425), and 25% validation (429). The model is initially developed using development data (427). The resulting performance on the test data (425) is used to monitor issues such as any over-fitting problems i.e., the model should exhibit comparable performance on both the development data (427) and test data (425). If a model has superior performance on development data (427) relative to test data (425), the model is adjusted until the model achieves stable performance.

To verify that the model will perform as expected on any independent dataset, ideally some fraction of the data are set aside solely for final model validation. A validation (or "hold-out") data set 429 consists of a set of example patterns that were not used to train the model. A completed model can then be used to score these unknown patterns, to estimate how the model might perform in scoring novel patterns.

Further, some applications may require an additional, "out-of-time" validation set, to verify the stability of model performance over time. Additional "data splitting" is often necessary for more sophisticated modeling methods, such as neural networks or genetic algorithms. For example, some modeling techniques require an "optimization" data set to monitor the progress of model optimization.

A further aspect of modeling is variable creation/transformations, as shown in step 430 of FIG. 4. In this processing, the objective is precision and the incorporation of domain knowledge. Raw data values do not necessarily make the best model variables due to many reasons: data input errors; non-numeric values; missing values; and outliers, for example. Before running the modeling logic, variables often need to be recreated or transformed to make the best usage from the information collected. To avoid the dependence between development data, test data and validation data, all the transformation logic will preferably be derived from development data only.

In conjunction with transforming the variables as desired and/or as needed, the modeling process includes the step 440 of variable selection. Thereafter, the model development may include training of the model 450 in conjunction with testing of the model. This may then be followed by model validation.

The results of the model validation 460 reveal whether performance objectives 470 were attained. As shown in FIG. 4, if the performance objectives have been attained, then the modeling process is terminated in step 480. Should the performance objectives not be attained, further development of the model may be required. Accordingly, the process of FIG. 4 may return to step 430 so as to vary the variable creation or transformations in order to achieve better performance.

Example 3

Plaque Classification

This example describes a preferred embodiment of the invention for detecting and classifying plaque using statistical classifiers. Initially, effort was directed to building a system using a set of models for detecting three key components of atherosclerotic plaque in MR (magnetic resonance) images of ex vivo blood vessels. The system also detected arterial muscle tissue that, when combined with the plaque and lipid detection systems, allowed the full artery to be identified in the image and plaque burden estimates to be computed. This system is fully automated, and in this example, the only human intervention in the detection and analysis process came during the collection of the raw magnetic resonance data from the MRI instrument. Using this system, a success rate equal or superior to the performance of a human expert radiologist was achieved in plaque component classification.

In this example, predictive models were trained to identify three tissue types: plaque, lipid, and muscle. The plaque detector was trained using a labeling of the example images that identified hard plaques. The lipid detector was trained on a smaller set of images where lipids could be identified and labeled. The muscle detector is used to separate arterial wall tissue from other parts of the vessel shown in the images. Additional models may be developed to detect calcified tissue, thrombus, and other non-pathological tissues. With a proper identification of the arterial walls it is possible to compute plaque burden estimates within the vessel given the outputs of the other models.

The goal of predictive modeling is to accurately predict the ground-truth classifications for each pixel of an image based on the characteristics of the MRI image at that pixel and its immediate surroundings. The predictive modeling began once the image processing steps were completed and the original images were transformed into columnar data representing each pixel as a record. Each pixel record contained one variable identifying the ground-truth classification for each pixel, and over four hundred additional variables capturing characteristics derived from the image processing steps. The challenge of the predictive modeling was to sift through these hundreds of potential variables, and thousands of permutations of the variables, to come up with the most predictive combination.

In a preferred embodiment, the artificial neural network (ANN) modeling approach known as the Relevant Input Processor Network (RIPNet™; Bates White, LLC, San Diego, Calif.; Perez-Amaral and White (2003), Oxford Bulleting of Economics and Statistics, vol. 65: 821-838); however, standard linear and non-linear regression techniques known to those in the art (such as linear and logistic regression, decision trees, non-parametric regression (e.g., using neural networks or radial basis functions), Bayesian network modeling, Fisher discriminant analysis, fuzzy logic systems, etc.) could also be used. RIPNet™ was developed specifically to address the problem of how to identify a network architecture with many potential variables, while avoiding overfit. The typical problem associated with neural network estimation is that the functional form embodied in these models is essentially "too flexible". Standard ANN approaches specify a level of model flexibility that, if left to be estimated automatically (unless a test or cross-validation process is also included automatically), summarize not only the signal in the data but the noise as well. This results in overfit, a situation in which the model does not generalize well for information not contained in the training data. Procedures such as optimal stopping rules have gained wide acceptance as a method for stopping the network training procedure (essentially a least-squares fitting algorithm) at a point before fitting of noise begins. These procedures deal with the symptom, but not the cause of model overfit. Model overfit in ANNs is fundamentally caused by an over-complexity in the model specification that is directly analogous to the overfit problems that may be encountered with linear models. When one encounters overfit in a linear model, one solution is not generally to modify the least squares fitting routine, but to simplify the model specification by dropping variables. Another solution is to use a cross-validation data set to indicate when to stop fitting.

RIPNet embodies a fundamentally different approach to neural network estimation that is aimed directly at identifying the level of model complexity that guarantees the best out-of-sample prediction performance without ad-hoc modifications to the fitting algorithms themselves. There are five major steps to producing models using the RIPNet approach, discussed in greater detail throughout the results sections that follow: (1) dataset creation, labeling, and sampling; (2) anomalous data detection; (3) variable pre-selection and transform generation; (4) predictive model estimation and variable selection; and (5) final model validation.

i. Dataset Creation.

The models were developed from pooled datasets of MRI images to predict the presence each of several major tissue features on a pixel-by-pixel basis. Ten labeled images yielded 112,481 useable tissue observations (i.e., pixels). The results demonstrate a scalable approach to feature detection that does not rely on the specifics of vessel geometry or the resolution of the image to obtain clinically relevant, reliable results.

The image data set used for model training and estimation consisted of ten ex vivo arterial sections that represent all of the arterial cross-section images available for this project. Labeling of the plaque, muscle, and lipid components of each artery was performed by direct comparison with histology. All images examined contained significant examples of hard plaque that was labeled for estimation. Muscle was clearly identifiable and labeled in most of the images, but in some, for example, the lower-quality image in FIG. 10, one of the arteries presents a histological challenge. Only three of the images contain examples of lipid, with the image in FIG. 5 having the largest such example.

The data extracted from these images was in the form of pixels that were treated as separate data points. The target variable for the modeling process is an indicator variable, which is one if the pixel belongs to the target class, and zero otherwise. This indicator is based on the labeling of the image. Associated with each pixel in the MRI image are three variables indicating intensity in the T1, T2, and PD modalities. The dynamic range of these intensities is 0 to 255, taking on only integer values (8 bit color depth). These data were heavily processed to generate a large number of additional variables summarizing such things as average intensity in the neighborhood of the pixel, and other more sophisticated transforms such as local texture measures.

Because the specimens were mounted on slides, which do not generate useful MRI information, a large number of pixels were dropped because they did not contain relevant data. Here, these pixels were identified as those for which the T1, T2, and PD indicator variables were all simultaneously zero. This procedure was conservative, and allowed some pixels with random noise into the dataset, although this has no impact on the performance of the algorithms. Over 50% of each original image was omitted in this way.

To maximize outcomes, the RIPNet procedure prefers that data be split at multiple stages in the modeling process so that there are systematic tests of real-world performance throughout. For this reason, some of the images were completely reserved as a test of performance. The datasets used for modeling were as follows: training, used to estimate model parameters; validation, used in the cross-validation of modeling results to verify performance of selected variables based on out-of-sample entropy measures and pseudo-R-squared measures; testing, only infrequently used for comparing the relative performance of alternative model specifications, this dataset was developed and used by the Data Miner's Reality Check™ algorithm (White, H. (2000), *Econometrica*, vol. 68:1097-1126; U.S. Pat. Nos. 5,893,069 and 6,088,676) because the validation dataset was heavily mined; and holdout, which data (three images and over 45,000 observations) was held entirely outside the estimation and validation processes in order to provide real-world examples to the model. All records were selected into their respective samples at random.

ii. Anomalous Data Detection.

An anomalous data detection algorithm was developed to identify outliers in the data. Here, the anomaly detector was a form of clustering algorithm that allows multivariate outliers to be identified among the data. An anomaly was identified as a record that is distant (as measured by L1-norm) from its k nearest neighbors. The data were separated between the target=0 sample and the target=1 sample so that anomalies could be identified relative to these separate groups. In this instance, k=10 was selected. This procedure typically is necessary to identify records that might have unusual leverage on the model estimation routines. However, if the image raw data from the imaging instrument is relatively clean, as is the case with most MRI data, no major outliers may be identified.

Table 2, below, set outs the contents of several anomaly variables

TABLE 2

| Anomaly variable contents | | |
|---|---|---|
| Plaque | Lipid | Muscle |
| PD mean 3 pixel radius | T1 min. 3 pixel radius | T2 min. 3 pixel radius |
| T2 mean 3 pixel radius | T2 min. 3 pixel radius | T1 min. 5 pixel radius |
| T2 median 3 pixel radius | T1 min. 4 pixel radius | T2 mean 5 pixel radius |
| T1 mean 5 pixel radius | T1 min. 5 pixel radius | T2 min. 5 pixel radius |
| k-means variable | T2 min. 5 pixel radius | k-means variable |

The anomalous data detection engine also generated an anomaly variable. The anomaly variable translated the two distance measures for each observation (relative to the target=0 sample and relative to the target=1 sample) into a likelihood ratio statistic. This statistic embeds relative distances to the target samples in a transformation of input variables, which is a powerful predictor in some instances. The anomaly variable for each model is composed of up to five continuous input variables, as shown in Table 2, above.

iii. Variable Pre-Selection and Transform Generation.

Next, an additional phase of variable transform generation and a preliminary elimination of non-predictive variables to reduce dataset sizes were undertaken. The transforms generated at this stage included the following for all of the variables on the input dataset: group transforms, which are univariate continuous variables grouped into decile bins that were then combined through a clustering algorithm to achieve the smallest number bins without significantly reducing predictive performance; cross-products, which are univariate continuous and discrete variables interacted with one another and grouped into binned categorical variables using the aforementioned clustering algorithm; and beta transforms, which are a flexible functional form based on fitting beta distribution functions to the data and computing likelihood ratios.

All of the variables generated up to this point were tested for performance on the target variable using an out-of-sample pseudo R-squared statistic. A straightforward entropy calculation contrasted the distributions of the independent variables given the state of the dependent variable, which was then summarized in a pseudo R-squared statistic for the validation sample. This pseudo R-squared statistic was not bounded between zero and one in small samples (because the domain is not precisely the same as for the estimation sample). The ten most predictive group transform variables and the ten most predictive cross-product variables were kept in the dataset and passed to the model estimation routine. Only the top five predictive beta transform variables were kept. Variables that had low or negative univariate or bivariate pseudo R-squared statistics were also permanently dropped from the potential candidate variable pool. These variable transforms are listed in Table 3, below.

TABLE 3

Variable Transforms

| Group transforms | Cross-products | Beta transforms |
| --- | --- | --- |
| anomaly | k-means × anomaly | anomaly |
| k-means | T2 mean 3 pix. rad × anomaly | k-means |
| T2 mean 3 pix. rad. | PD 3 pix. prep × anomaly | T2 mean 3 pix. rad. |
| T2 med. 3 pix. rad. | T2 median 3 pix. rad × anomaly | T2 med. 3 pix. rad. |
| PD 3 pixel preprocessing | T2 mean 3 pix. rad × k-means | pd 3 pix. preproc. |
| T1 mean 5 pix. rad. | T2 median 3 pix. rad × k-means | |
| T1 med. 5 pix. rad. | PD 3 pix. prep × k-means | |
| T2 med. 5 pix. rad. | PD 3 pix. prep × T2 mean 3 pix. rad | |
| yellow colorspace | T2 med. 3 pix. rad × T2 mean 3 pix. rad | |
| PD 5 pix. prep. | PD 3 pix. prep × T2 med. 3 pix. rad | | iv. Model Estimation and Variable Selection.

As with most pattern recognition examples, there were far more potential candidate variables for inclusion than could practically be accommodated in a predictive model, which poses several significant risks. One is that potentially useful candidates are overlooked simply because there are too many variables to evaluate. Another is that if a systematic routine for evaluating and including variables is used, it can lead to overfitting. Finally, many candidate variables are likely to be redundant, which can cause problems for the estimation routines. For example, the mean of the T1 modality was taken over neighborhoods ranging from a 3-pixel radius to a 9-pixel radius, and all were included as candidate variables.

The RIPNet™ procedure used in this example deals with these risks by combining the theoretical nonlinear curve fitting capability of the typical ANN with the stability of hierarchical techniques. This search over nonlinear combinations and transformations of input variables can then be used in a standard maximum likelihood logit model. RIPNet™ contains algorithms for variable generation (network nodes), variable testing, and model estimation.

A typical single hidden layer feed-forward network may have two inputs and one output and use so-called squashing (s-shaped) functions. These squashing functions deliver the power of ANNs because they exhibit several different behaviors depending on the settings of the parameters $\beta$ and $\gamma$. Examples of such settings include: inverse; logarithmic; exponential; and threshold functions.

The RIPNet modeling strategy starts with a functional form whose richness and nonlinearity stem from the functions. Among the key contributions of the RIPNet algorithm is a high-yield method for generating simulated network nodes. In spite of its outward simplicity, this form of model can be used to closely approximate the performance of traditional ANNs.

Node selection within a class of relatively tractable models is the next step in the process. As with the variable pre-filtering steps, node selection was based upon the use of a validation sample to check out-of-sample performance. Candidate nodes were entered into the model in order of their validated prediction performance in a predictive model. Redundancy was handled in two ways within the selection procedure. First, as additional nodes were entered into the model, they are orthogonalized so as to remove redundant components. Multiple thresholds were tested so that an optimal level of node orthogonality could be identified. Second, a threshold for redundancy was picked such that only nodes with less than 5% of their variance explained by other nodes in the model could be entered.

v. Model Validation.

A final model validation step was used to ensure that whichever model was selected as the final model, it was better than a simpler benchmark or other candidate models. Data Miner's Reality Check™ (DMRC) was again used to test the models in this way. This technique utilized out of sample predictions and bootstrap distributions to generate valid p-values for the hypothesis that the tested model had the same performance as the benchmark model. Low p-values indicated that the tested model exhibited significantly better performance.

vi. Results.

Figure 9:
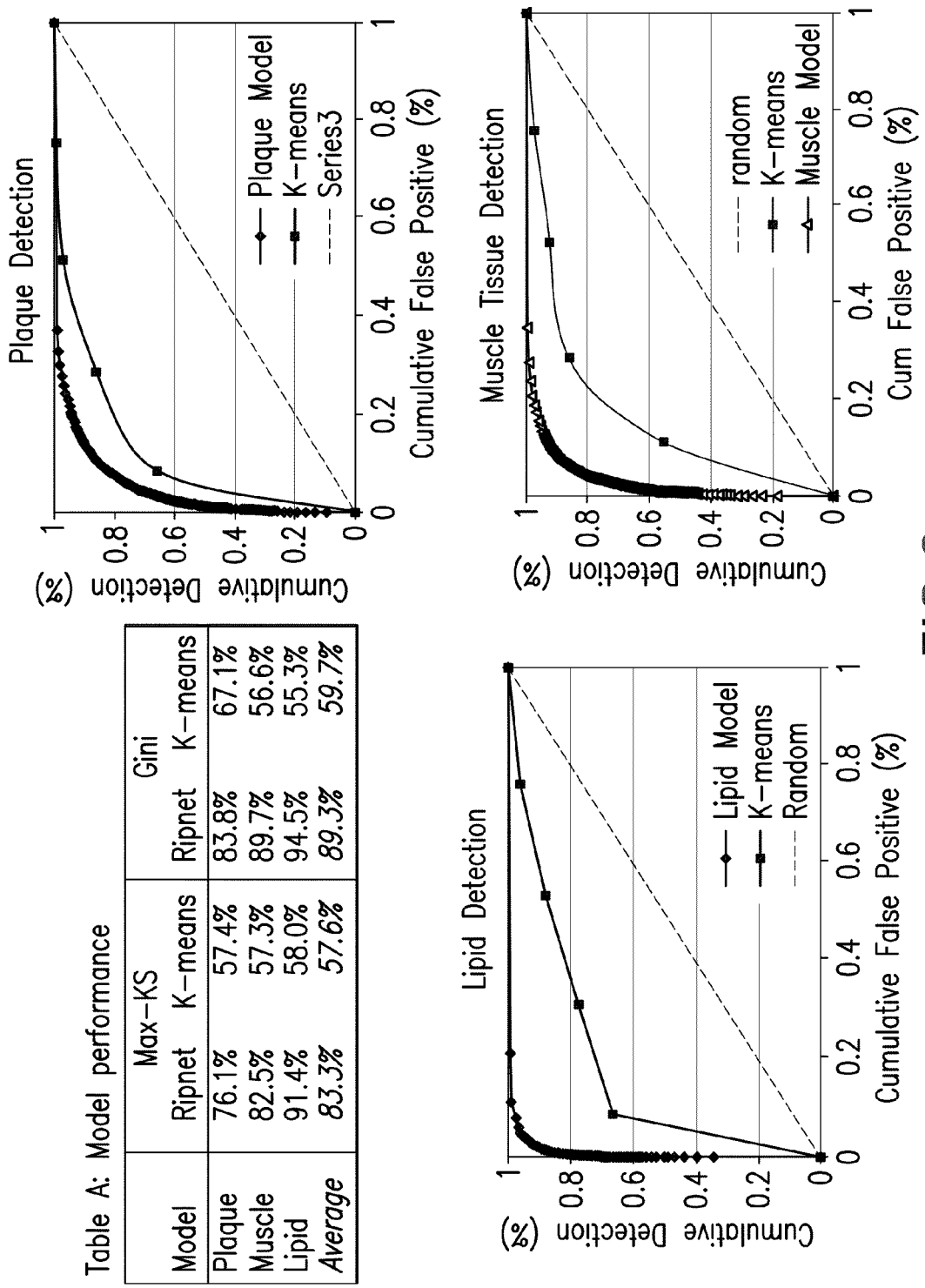
FIG. 9 contains a table (Table A) and three graphs summarizing the performance of three predictive models for detecting vascular plaque, a component thereof (i.e., lipid), and muscle tissue. Table A shows the performance of the RIPNet models based on the maximum Kolmogorov-Smirnov statistic (Max-KS) and the Gini coefficient measurements of the ROC curves shown elsewhere in the figure.

The predictive models described herein have significantly improved predictive performance relative to the leading techniques in use today. FIG. 9 summarizes the performance of the models described above. In the figure, Table A summarizes the performance of the RIPNet models based on two different statistical measures: the maximum Kolmogorov-Smirnov statistic; and the Gini coefficient, each of which measure aspects of the ROC (regional operational characteristics) curve. Models based on the K-means approach are used as a basis for comparison. These results demonstrate that the RIPNet models universally perform between 25% and 30% better in absolute terms than K-means. This translates to a 50% higher true positive rate a given level of false positives. The ROC curves from which these results were derived are shown in FIG. 9.

In addition to statistical performance measures, the combined model results shown in image form (FIG. 8) also support this conclusion. In FIG. 8, for each image the labeled ground-truth is presented in the left panel, and the modeling predictions for the same image are presented in the right panel. In the figure, muscle appears pink in the labeled images, and red in the model results. Lipids appear white in the labeled images, and blue in the model results, while plaque appears yellow in both images. Each pixel was assigned to a category depending on which model generated the highest probability for that pixel. Pixels with below 30% probability for all of the model predictions were coded as blank.

Figure 8A:
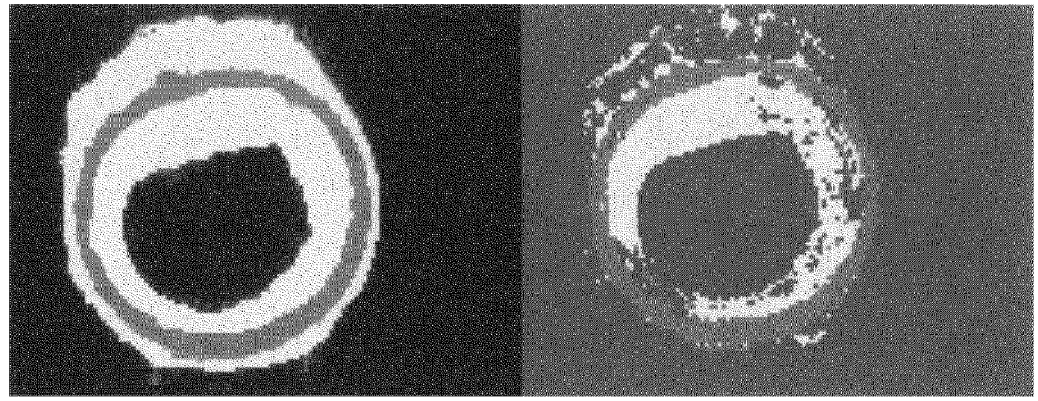
FIG. 8 has two panels, A and B, illustrating the performance of a preferred embodiment as measured against labeled ground truth (left portion of each panel).
Figure 8B:
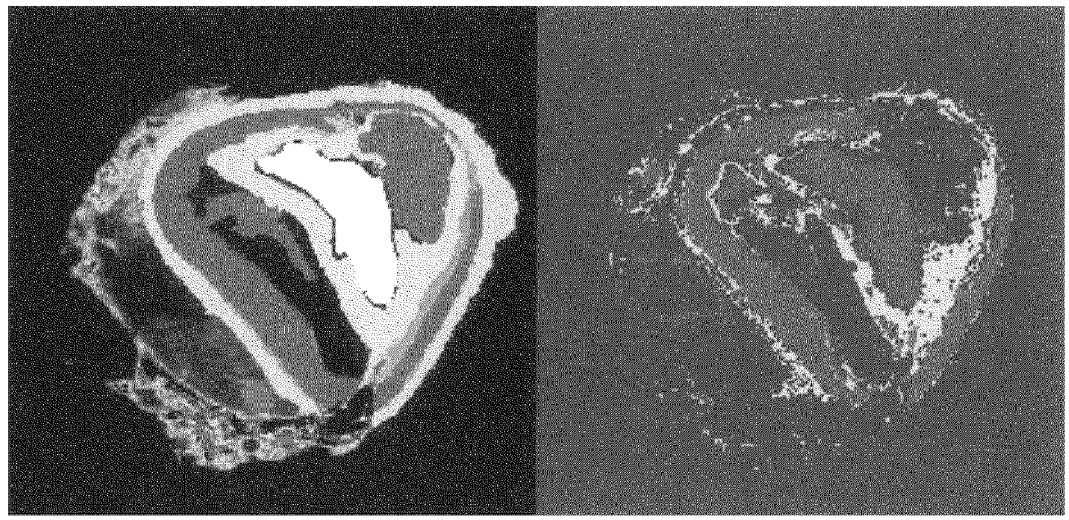

The image developed from the predictive model shown in FIG. 8A provides a clear example of the capabilities of the predictive models of the invention. In particular, there is a high degree of correspondence between the pixels labeled plaque in the original, ground-truth, labeled image, and those labeled plaque by the computational models. Likewise, muscle was also well identified. The image in FIG. 8B demonstrates the ability of the models of the invention to detect not only the hard vascular plaques, but also plaques having lipid components. The muscle areas are not uniformly identified, but this occurs in precisely those areas where the original image is plagued by artifacts and where the muscle wall is thin. Interestingly, there are some false-positives coming from the muscle model along areas of the fibrous cap enclosing the lipid core shown in this image.

Over 400 variables were included in this analysis, and thousands of network nodes were created from these variables. Out of all of these nodes, 140 were selected for each model. This would normally be considered a large number, but for the large number of observations in the datasets. Table 4, below, illustrate the top several nodes selected for each model. An examination of these nodes illustrates the benefits of using an automated technique over other approaches. For example, the plaque model contains mainly T1 and PD variables, and for almost all of the included variables a 7-pixel neighborhood measure was selected over all of the others available. These types of selections would have been almost impossible to reproduce manually without enormous effort. Likewise, many of the combinations of variables are not obvious to the human eye. For example, the top node for the lipid model is a linear combination of the maximum of the four-pixel neighborhood for T2, the discrete cosine transform of PD, and the anomaly variable—combinations for which no clear explanation exists today. Certainly none of the usual heuristic methods would have uncovered these.

TABLE 4

Top Relevant Inputs

| Rank | Type | Description |
|---|---|---|
| | | Plaque Model |
| 1 | Node | Kmeans |
| 2 | Node | T1 Mean of 7 pix rad. |
| 3 | Node | PD Median of 7 pix rad |
| 4 | Node | T1 Min of 3 pix rad |
| 5 | Node | T1 Min of 7 pix rad |
| 6 | Node | PD DCT of 7 pix rad |
| | | Muscle Model |
| 1 | Node | Anomaly |
| 2 | Node | Anomaly<br>T2 Var. 4 pix rad |
| 3 | Node | Anomaly<br>PD Skew. 3 pix rad |
| 4 | Hidden Unit | T1 Pre-proc. 3 pix rad<br>T2 Pre-proc. 5 pix rad<br>CR<br>PD DCT of 7 pix rad<br>Anomaly variable |
| | | Lipid Model |

TABLE 4-continued

Top Relevant Inputs

| Rank | Type | Description |
|---|---|---|
| 1 | Hidden Unit | T2 Max of 4 pix rad<br>PD DCT 5 pix rad<br>Anomaly |
| 2 | Hidden Unit | T1 Mean of 3 pix rad<br>PD Max of 3 pix rad<br>Yellow - CMYK transform<br>PD DCT of 5 pix rad<br>Anomaly variable |
| 3 | Hidden Unit | T2 Range of 3 pix rad<br>PD Variance of 4 pix rad<br>PD IQR of 5 pix rad<br>PD DCT of 6 pix rad<br>Anomaly |

It is important to note also the highly non-linear nature of these models. The fact that the anomaly variable appears as one of the most predictive variables serves to underscore this fact. Hidden units, the group transforms, the beta transforms, etc. are all non-linear transformations of the inputs that appear as top-ranked variables in these models.

Figure 10C:
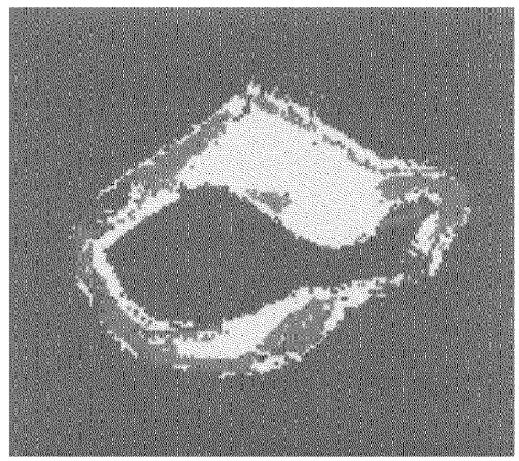
FIG. 10 has three panels, A-C, showing performance of a preferred embodiment of the invention on a low-quality image held out of the model development process.
Figure 10B:
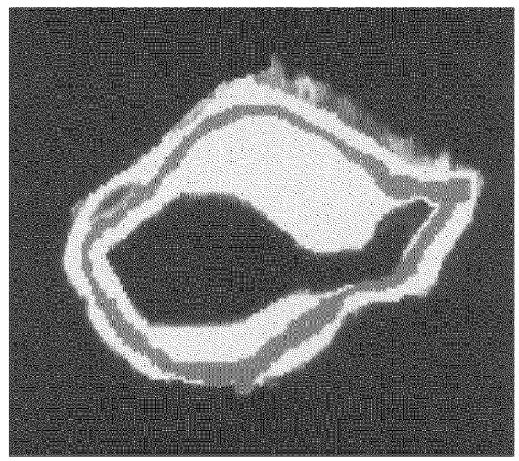
Figure 10A:
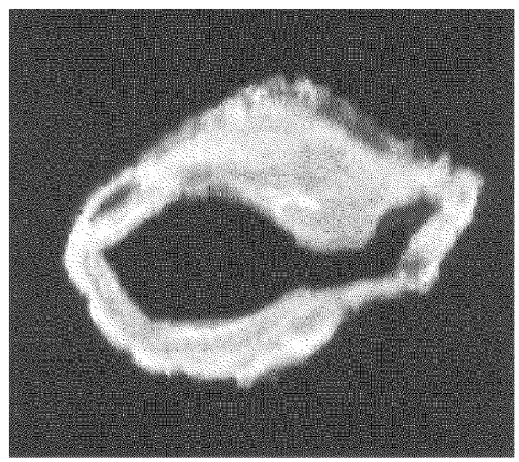

To avoid overfit, precautions were taken. Testing was performed on several images that were reserved entirely from the modeling process. As shown in FIG. 10, the models do a reasonably good job separating muscle from plaque. The muscle model tracks the general outline of the artery wall, and the model identifies the labeled plaque areas well. As this image was challenging for expert radiologists to label in the first place, it made for a challenging, and ultimately successful, test.

Example 4

3-D Blood Vessel Models

Figure 13:
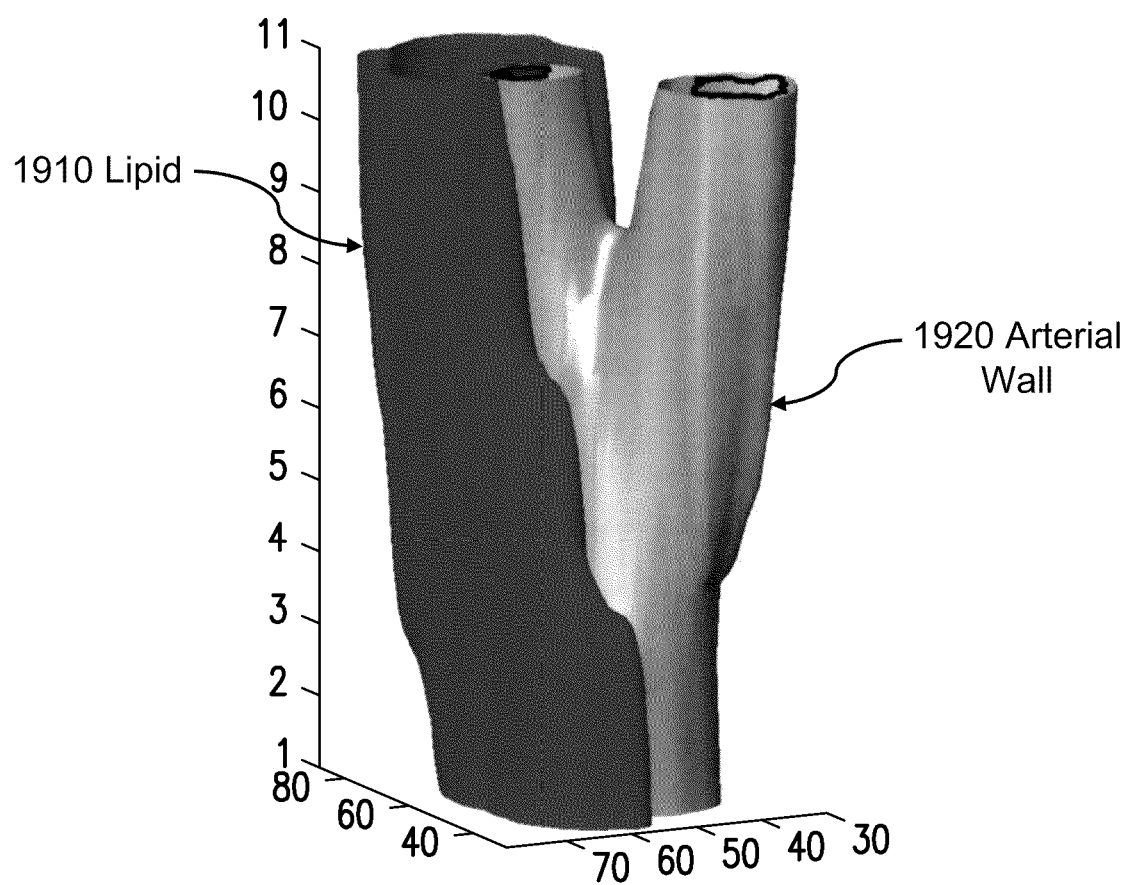
FIG. 13 shows the three-dimensional of part of carotid artery, in the region of the carotid bifurcation. In the model, the interior boundary of the arterial wall (1920) and hard plaque (1930) within the vessel lumen (1940) is shown, while the exterior boundary of the artery is not shown. Lipid (1910) between the interior surface (1920) and exterior surface of the artery wall (not shown) is shown in red. The hard plaque in the model is colored beige.

This example describes a preferred method for generating three-dimensional models of blood vessels that have been imaged using a medical imaging instrument. Specifically, FIG. 13 shows a 3-D rendering of a carotid artery in the area of the carotid bifurcation. In the figure, the inner arterial wall (1920) represents the boundary of the lumen. Plaque (1910) resides between the inner surface of the arterial wall and the exterior surface of the artery (not shown). This model was derived from eleven in vivo MRI tissue slices using only the T1 mode. In order to generate the model, the following steps were used transform the tissue slice images. Initial, the data for each slice was passed through a low pass filter (e.g., adaptive Wiener filter). The location of the lumen center for each slice was estimated based on the position of the lumen centroid from the preceding slice. Each image was then cropped after centering on the estimated lumen location. A linear search of threshold intensities was then performed to reveal lumen area close to the estimated centroid. After verifying that the lumen had the requisite morphological features, including area and eccentricity, the position of the lumen centroid was re-estimated. Tissue segmentation was then performed to identify lipid features near the lumen centroid.

As will be appreciated, the foregoing process was modified slightly depending on whether the slice was above or below the carotid bifurcation. When the algorithm was tracking two lumens (i.e., in slices above the carotid bifurcation), the geometric mean of the two lumen centroids were used. The resulting slices were then re-centered in order to compensate for axial misalignment. The addition of other tissue information, including that for muscle, adventitia, and plaque components such as lipid, hemorrhage, fibrous plaque, and calcium, can also be included. The resulting models will allow for visualization and automated quantification of plaque size, volume, and composition.

All of the processes, systems, and articles of manufacture described and claimed herein can be made and executed without undue experimentation in light of this specification. While the methods, systems, and computer program products of the invention have been described in terms of preferred embodiments and optional features, it will be apparent to those of skill in the art that modifications and variations may be applied to the methods and in the steps or in the sequence of steps of the methods described herein without departing from the spirit and scope of the invention. More specifically, it will be apparent that different algorithms, software, and data can be adapted for the automated detection and analysis of vascular plaque. All such equivalent or similar adaptations, embellishments, modifications, and substitutes apparent to those skilled in the art are deemed to be within the spirit and scope of the invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

The invention illustratively described herein suitably may be practiced in the absence of any element(s) not specifically disclosed herein as essential. The terms and expressions which have been employed are used as terms of description and not of limitation, and there is no intention that in the use of such terms and expressions of excluding any now-existing or later-developed equivalents of the features shown and described or portions thereof, but it is recognized that various modifications are possible within the scope of the invention claimed. Also, the terms "comprising", "including", "containing", etc. are to be read expansively and without limitation. It must be noted that as used herein and in the appended claims, the singular forms "a", "an", and "the" include plural reference unless the context clearly dictates otherwise.

All patents, patent applications, and publications mentioned in this specification are indicative of the levels of those of ordinary skill in the art to which the invention pertains. All patents, patent applications, and publications are herein incorporated by reference in their entirety for all purposes and to the same extent as if each individual patent, patent application, or publication was specifically and individually indicated as being incorporated by reference.

We claim:

1. A fully automated method of classifying plaque components to determine whether a blood vessel contains plaque, the method comprising computationally processing at least a first processable data type and a second processable data type obtained using at least one non-invasive medical imaging system in order to analyze at least one cross section of a blood vessel of a patient's vasculature using a plurality of stored tissue classifier elements developed using statistical modeling to determine if the blood vessel comprises at least one tissue correlated with the presence of plaque, in which event the blood vessel is determined to contain plaque, wherein the fully automated method does not require human intervention and wherein at least one of the first and second processable data types is processable magnetic resonance data generated by an MRI instrument.

2. A fully automated method according to claim 1 wherein the blood vessel comprises a portion of the vasculature supplying blood to an organ selected from the group consisting of a brain and a heart, wherein when the brain is the organ the blood vessel is a carotid artery and wherein when the heart is the organ the blood vessel is a coronary artery, further wherein the patient is human.

3. A fully automated method according to claim 1 wherein the processable data are generated by pre-processing raw data generated by the medical imaging system.

4. A fully automated method according to claim 3 further comprising normalizing the processable data prior to computationally processing the processable data.

5. A fully automated method according to claim 1 wherein the plurality of stored tissue classifier elements are developed using known outcome data by a process selected from the group consisting of logistic regression, decision trees, nonparametric regression, Fisher discriminant analysis, Bayesian network modeling, and a fuzzy logic system.

6. A fully automated method according to claim 5 wherein at least one of the plurality of stored tissue classifier elements is determined by a process selected from the group consisting of post-operative histological examination, direct tissue inspection, and labeling by one or more experts.

7. A fully automated method according to claim 1 further comprising at least one of the following:
  a. computationally processing the processable data to determine whether the blood vessel, in the region of the cross section, further comprises at least one tissue selected from the group consisting of adventitia, a calcium deposit, a cholesterol deposit, fibrous plaque, and thrombus;
  b. computationally processing the processable magnetic resonance data into registration, wherein the registration is accomplished by aligning components derived from the processable magnetic resonance data about a representation that represents a landmark selected from the group consisting of a physical landmark and a computational landmark, wherein the physical landmark is a vessel branch point vessel and the computational landmark is a lumen centroid;
  c. computationally processing processable data of a plurality of spaced cross sections of the blood vessel;
  d. computationally processing processable data of a plurality of spaced cross sections of the blood vessel and computationally rendering a three-dimensional model of the blood vessel over at least a portion of a region bounded by most distantly spaced cross sections of the blood vessel;
  e. generating an output file comprising data resulting from the computationally processing, wherein the output file comprises a computationally rendered three-dimensional model of the blood vessel over at least a portion of a region bounded by most distantly spaced cross sections of the blood vessel;
  f. computationally processing processable data of a plurality of spaced cross sections of the blood vessel, computationally rendering a three-dimensional model of the blood vessel over at least a portion of a region bounded by most distantly spaced cross sections of the blood vessel, and computationally determining plaque volume present in the three-dimensional model of the blood vessel;
  g. computationally processing processable data of a plurality of spaced cross sections of the blood vessel, computationally rendering a three-dimensional model of the blood vessel over at least a portion of a region bounded by most distantly spaced cross sections of the blood vessel, and computationally determining composition of plaque present in the three-dimensional model of the blood vessel; and h. computationally processing processable data of a plurality of spaced cross sections of the blood vessel, computationally rendering a three-dimensional model of the blood vessel over at least a portion of a region bounded by most distantly spaced cross sections of the blood vessel, and computationally determining composition of plaque present in the three-dimensional model of the blood vessel and distinguishing whether the plaque is a vulnerable plaque or a stable plaque.

8. A fully automated method of assessing effectiveness of a therapeutic regimen, comprising:

a. determining a plaque volume in at least a portion of a blood vessel of a patient using a fully automated method according to claim 1;

b. delivering to the patient a therapeutic regimen comprising administration of a drug expected to stabilize or reduce plaque volume over the course of the therapeutic regimen; and c. during and/or at the end of the therapeutic regimen determining whether the plaque volume has stabilized or been reduced, thereby allowing assessment of the effectiveness of the therapeutic regimen.

9. A fully automated method for determining whether a blood vessel of a patient contains plaque, comprising:

a. obtaining processable data of at least one cross section of a blood vessel of a patient's vasculature, wherein the processable data are derived from raw data collected using a non-invasive medical imaging system that comprises an MRI instrument, wherein the processable data comprises at least a first processable magnetic resonance data type and a second processable magnetic resonance data type generated by an MRI instrument; and b. communicating the processable data to a computer configured to receive and computationally process the processable data using statistical classifiers developed using statistical modeling to determine whether the blood vessel in a region of the cross section(s) comprises at least one tissue correlated with the presence of plaque, in which event the blood vessel is determined to contain plaque;

wherein the computational processing and determination of whether the blood vessel contains plaque does not require human intervention.

10. A fully automated method according to claim 9 wherein the blood vessel comprises a portion of the vasculature supplying blood to an organ selected from the group consisting of a brain and a heart, wherein when the brain is the organ the blood vessel is a carotid artery and wherein when the heart is the organ the blood vessel is a coronary artery, further wherein the patient is human.

11. A fully automated method according to claim 9 wherein the non-invasive medical imaging system and the computer are located at different locations.

12. A fully automated method according to claim 9 wherein the computer resides in a computational center physically removed from each of a plurality of imaging centers, each of which imaging centers comprises a non-invasive medical imaging system capable of generating raw magnetic resonance data from which processable magnetic resonance data can be derived, wherein at least one of the imaging centers communicates raw data to the computational center via a telecommunications link.

13. A fully automated method according to claim 9 further comprising communicating results of the computational processing and determination of whether the blood vessel contains plague to an address specified as being affiliated with the non-invasive medical imaging system used to collect the raw data.

* * * * *